(12) United States Patent
Wan et al.

(10) Patent No.: US 11,583,609 B2
(45) Date of Patent: Feb. 21, 2023

(54) COLLAGEN CONSTRUCTS AND METHODS OF MAKING THE SAME

(71) Applicant: MiMedx Group, Inc., Marietta, GA (US)

(72) Inventors: Chen-rei Wan, Smyrna, GA (US); Thomas J. Koob, Kennesaw, GA (US); Kirk Joseph Naizer, Dunwoody, GA (US)

(73) Assignee: MiMedx Group, Inc., Marietta, GA (US)

( * ) Notice: Subject to any disclaimer, the term of this patent is extended or adjusted under 35 U.S.C. 154(b) by 282 days.

(21) Appl. No.: 16/534,449

(22) Filed: Aug. 7, 2019

(65) Prior Publication Data
US 2020/0046872 A1 Feb. 13, 2020

Related U.S. Application Data

(60) Provisional application No. 62/716,103, filed on Aug. 8, 2018.

(51) Int. Cl.
*A61L 17/08* (2006.01)
*A61B 17/06* (2006.01)
*D01F 4/00* (2006.01)

(52) U.S. Cl.
CPC ........ *A61L 17/08* (2013.01); *A61B 17/06166* (2013.01); *D01F 4/00* (2013.01)

(58) Field of Classification Search
CPC ...... A61L 17/08; A61B 17/06166; D01F 4/00
See application file for complete search history.

(56) References Cited

U.S. PATENT DOCUMENTS

| | | | |
|---|---|---|---|
| 4,047,533 A * | 9/1977 | Perciaccante | A61B 17/06166 606/230 |
| 4,605,414 A | 8/1986 | Czajka | |
| 4,883,486 A | 11/1989 | Kapadia et al. | |
| 4,979,956 A | 12/1990 | Silvestrini | |
| 5,329,846 A | 7/1994 | Bonutti | |
| 5,378,469 A | 1/1995 | Kemp | |
| 5,521,087 A | 5/1996 | Lee et al. | |
| 5,718,012 A | 2/1998 | Cavallaro | |
| 5,814,328 A | 9/1998 | Gunasekaran | |
| 6,045,571 A * | 4/2000 | Hill | A61B 17/06166 606/228 |
| 6,162,537 A * | 12/2000 | Martin | D01F 8/16 428/373 |
| 6,565,960 B2 | 5/2003 | Koob | |
| 6,821,530 B2 | 11/2004 | Koob | |

(Continued)

FOREIGN PATENT DOCUMENTS

WO 9614095 A1 5/1996

*Primary Examiner* — Alexander J Orkin
(74) *Attorney, Agent, or Firm* — Myers Bigel, P.A.

(57) ABSTRACT

The present disclosure describes a medical construct. The medical construct includes a first layer comprising an array of collagen fibers, the first layer forming a core of the medical construct, and a second layer comprising a plurality of braided collagen fibers, wherein the second layer surrounds the core of the medical construct. In some embodiments, the medical construct may further include a third layer comprising a plurality of braided collagen fibers, wherein the third layer surrounds the second layer. Methods of manufacturing a medical construct also provided.

19 Claims, 16 Drawing Sheets

(56) References Cited

U.S. PATENT DOCUMENTS

| | | |
|---|---|---|
| 8,177,839 B2 | 5/2012 | Koob |
| 8,367,148 B2 | 2/2013 | Greenhalgh |
| 8,858,633 B2 | 10/2014 | Koob |
| 8,940,684 B2 | 1/2015 | Koob |
| 8,946,163 B2 | 2/2015 | Koob |
| 8,986,378 B2 | 3/2015 | Koob |
| 9,005,285 B2 | 4/2015 | Niu |
| 9,078,775 B2 | 7/2015 | Li |
| 9,125,759 B2 | 9/2015 | Greenhalgh |
| 9,155,799 B2 | 10/2015 | Koob |
| 9,179,976 B2 | 11/2015 | Paulos |
| 9,216,077 B2 | 12/2015 | Davis |
| 9,393,105 B2 | 7/2016 | Koob |
| 9,603,968 B2 | 3/2017 | Koob |
| 9,610,151 B2 | 4/2017 | Niu |
| 9,636,209 B2 | 5/2017 | Koob |
| 9,681,869 B2 | 6/2017 | Wiedrich |
| 9,694,106 B2 | 7/2017 | Brown |
| 9,801,978 B2 | 10/2017 | Paulos |
| 9,873,861 B2 | 1/2018 | Koob |
| 9,888,996 B2 | 2/2018 | Koob |
| 10,149,918 B2 | 12/2018 | Davis |
| 10,238,773 B2 | 3/2019 | Li |
| 10,258,327 B2 | 4/2019 | Wiedrich |
| 11,008,676 B2 * | 5/2021 | Chadha ................. D03D 27/04 |
| 2002/0072806 A1 | 6/2002 | Buskirk et al. |
| 2004/0267316 A1 * | 12/2004 | Powell ............. A61B 17/06166 |
| | | 606/231 |
| 2005/0033362 A1 * | 2/2005 | Grafton ................. A61L 17/145 |
| | | 606/228 |
| 2006/0155328 A1 * | 7/2006 | Foerster ................. D07B 1/025 |
| | | 606/228 |
| 2008/0161917 A1 | 7/2008 | Koob et al. |
| 2009/0287308 A1 * | 11/2009 | Davis ................... A61B 17/562 |
| | | 623/13.12 |
| 2010/0063599 A1 * | 3/2010 | Brunelle ............... A61L 31/145 |
| | | 623/23.72 |
| 2010/0094318 A1 * | 4/2010 | Li ........................... B32B 37/20 |
| | | 606/152 |
| 2012/0232589 A1 * | 9/2012 | Fedinec ................... D04C 1/12 |
| | | 606/228 |
| 2013/0211430 A1 * | 8/2013 | Egnelov .................. A61L 17/06 |
| | | 606/151 |
| 2013/0226232 A1 * | 8/2013 | Dumanian ............. A61B 17/06 |
| | | 606/224 |
| 2013/0231700 A1 * | 9/2013 | Gedet ............... A61B 17/06166 |
| | | 606/228 |
| 2014/0172096 A1 * | 6/2014 | Koob ............... A61B 17/06166 |
| | | 139/35 |
| 2017/0152301 A1 | 6/2017 | Koob |
| 2017/0189163 A1 | 7/2017 | Koob |
| 2017/0266341 A1 | 9/2017 | Brown |
| 2018/0127711 A1 * | 5/2018 | Koob |
| 2018/0168797 A1 | 6/2018 | Koob |
| 2018/0177921 A1 | 6/2018 | Paulos |
| 2019/0029680 A1 * | 1/2019 | Rustamova ....... A61B 17/06166 |
| 2019/0350690 A1 * | 11/2019 | Koob ...................... A61L 27/24 |

\* cited by examiner

COLLAGEN CONSTRUCTS AND METHODS OF MAKING THE SAME

RELATED APPLICATION

The present application claims priority from and the benefit of U.S. Provisional Application Ser. No. 62/716,103 filed Aug. 8, 2018, the disclosure of which is hereby incorporated herein in its entirety.

FIELD OF THE INVENTION

The invention relates to constructs including collagen, such as collagen sutures, and methods of making the same.

BACKGROUND OF THE INVENTION

Methods and uses of collagen fibers to make various medical constructs are known. See, for example, U.S. Pat. Nos. 8,367,148; 9,125,759; and 9,078,775, and U.S. Patent Publication No. 2015/0283305, the contents of each of which are hereby incorporated by reference in their entirety as if recited in full herein.

SUMMARY OF THE INVENTION

A first aspect of the present invention is directed to a construct, such as, for example a medical construct. The construct may comprise a first layer comprising an array of collagen fibers. The first layer may form a core of the construct. The construct may further comprise a second layer comprising a plurality of braided collagen fibers. The second layer may surround the core of the construct. The construct may further comprise a third layer. The third layer may comprise a third plurality of braided collagen fibers where the third layer surrounds the first layer and the second layer. The construct may further comprise a needle attached to at least one end of the construct.

The array of collagen fibers may comprise a plurality of collagen fibers. Each collagen fiber of the plurality of collagen fibers may extend substantially parallel to each other along a longitudinal axis of the first layer. The plurality of braided collagen fibers may be a first plurality of braided collagen fibers, and the array of collagen fibers may comprise a second plurality of braided collagen fibers.

The first plurality and/or second plurality of braided collagen fibers may be braided in a repeating braid pattern in which each collagen fiber of the plurality passes over one collagen fiber and under one collagen fiber. The first plurality and/or second plurality of braided collagen fibers may be braided in a repeating braid pattern in which each collagen fiber of the plurality passes over two collagen fibers and under two collagen fibers. The first plurality and/or the second plurality of braided collagen fibers may comprise paired or non-paired collagen fibers. The collagen fibers in the first and/or second plurality of braided collagen fibers may be arranged in an alternating braid pattern.

The first plurality and/or second plurality of braided collagen fibers may comprise at least one chase fiber. The first plurality and/or second plurality of braided collagen fibers may comprise at least one tri-axe fiber.

The first plurality and/or second plurality of braided collagen fibers may comprise a first, second, and third collagen fiber with the second collagen fiber being between the first and third collagen fibers, and the first, second and third collagen fibers may be braided together to form a braid. The braid may comprise a portion in which the first and second collagen fibers form a pick under a crossing collagen fiber, and the third collagen fiber passes over the crossing collagen fiber, and a portion in which the second and third collagen fibers form a pick under the crossing collagen fiber, and the first collagen fiber passes over the crossing collagen fiber. The first and third collagen fibers may be arranged in an alternating braid pattern.

The first plurality of braided collagen fibers may have a greater number of picks per inch than the second plurality of braided collagen fibers. The plurality of braided collagen fibers may be braided at about 5 picks per inch to about 40 PPI picks per inch.

The first layer of the construct may comprise 4 collagen fibers and the second layer may comprise 16 collagen fibers. The first layer and/or the second layer may comprise about 1 collagen fiber to about 25 collagen fibers.

The construct may further comprise a third layer. The third layer may comprise a third plurality of braided collagen fibers. The third layer may surround the first layer and the second layer. Optionally, the third layer may have a greater number of picks per inch than the first plurality and/or the second plurality of braided collagen fibers.

The first plurality, second plurality, and/or third plurality of braided collagen fibers may be braided in a repeating braid pattern in which each collagen fiber of the plurality passes over one collagen fiber and under one collagen fiber. The first plurality, second plurality, and/or third plurality of braided collagen fibers may be braided in a repeating braid pattern in which each collagen fiber of the plurality passes over two collagen fibers and under two collagen fibers.

The first plurality, second plurality, and/or third plurality of braided collagen fibers may comprise paired or non-paired collagen fibers. The collagen fibers in the first plurality, second plurality, and/or third plurality of braided collagen fibers may be arranged in an alternating braid pattern.

The first plurality, second plurality and/or third plurality of braided collagen fibers may comprise at least one chase fiber. The first plurality, second plurality, and/or third plurality of braided collagen fibers may comprise at least one tri-axe fiber.

The first layer of the construct may comprise 12 collagen fibers, the second layer may comprise 16 collagen fibers, and the third layer may comprise 16 collagen fibers. The first layer of collagen fibers may be braided at about 5 picks per inch, the second layer of collagen fibers may be braided at about 15 picks per inch, and the third layer of collagen fibers may be braided at about 20 picks per inch.

The construct may comprise about 10 collagen fibers to about 60 collagen fibers. The construct may have a diameter of about 0.1 mm to about 1.5 mm. The construct may have a tensile strength of about 10 N to about 50 N. The construct may have a flexural stiffness of about $3 \times 10^6$ kg/cm$^2$ to about 1 kg/cm$^2$.

The collagen fibers of the construct may have a length of about 40 cm to about 100 m. One or more of the collagen fibers in the first plurality, second plurality, and/or third plurality may each have a tensile strength of about 0.5 N to about 5 N. Optionally, on average, the collagen fibers in the first, second, and/or third plurality may have a tensile strength of about 1.5 N to about 3.5 N. The construct may have a length of about 30 cm to about 100 cm.

The construct may further comprise a coating applied to the first plurality, second plurality, and/or third plurality of braided collagen fibers. The coating may comprise polylactic acid.

When the construct is implanted, cell ingrowth may occur in the first plurality, second plurality, and/or third plurality of braid collagen fibers between Day 0 and Day 7 as measured ex vivo using Hematoxylin and Eosin staining of resected and fixed specimens.

Another aspect of the present invention is directed to a method of manufacturing a construct. The method may comprise the steps of providing a first plurality of collagen fibers and braiding a second plurality of collagen fibers around the first plurality of collagen fibers, thereby forming the construct. The method may further comprise braiding a third plurality of collagen fibers around the second plurality of collagen fibers.

Each collagen fiber of the first plurality of collagen fibers may extend substantially parallel to each other along a longitudinal axis of the construct. The first plurality of collagen fibers may be braided together. The second plurality of collagen fibers may be braided at about 5 picks per inch to about 40 picks per inch.

The method may further comprise braiding a third plurality of collagen fibers around the second plurality of collagen fibers.

The first plurality, second plurality, and/or third plurality of braided collagen fibers may be braided in a repeating braid pattern in which each collagen fiber of the first, second, and/or third plurality passes over one collagen fiber and passes under one collagen fiber. The first plurality, second plurality, and/or third plurality of braided collagen fibers may be braided in a repeating braid pattern in which each collagen fiber of the first, second, and/or third plurality passes over two collagen fibers and passes under two collagen fibers. The first plurality, second plurality, and/or third plurality of braided collagen fibers may comprise paired or non-paired collagen fibers. The collagen fibers in the first plurality, second plurality, and/or third plurality of braided collagen fibers may be arranged in an alternating braid pattern.

The first and/or second plurality of braided collagen fibers may comprise at least one chase fiber. The first and/or second plurality of braided collagen fibers may comprise at least one tri-axe fiber.

The first plurality of collagen fibers may be held in tension while the second plurality of collagen fibers is braided around the first plurality of collagen fibers, optionally at a tension of about 5% to about 30%. The first plurality of collagen fibers may be held in tension while the third plurality of collagen fibers is braided around the second plurality of collagen fibers, optionally at a tension of about 40% to about 100%.

The first plurality of collagen fibers may be braided at about 5 picks per inch, the second plurality of collagen fibers may be braided at about 15 picks per inch, and the third plurality of collagen fibers may be braided at about 20 picks per inch.

The method may further comprise attaching a needle to at least one end of the construct.

A further aspect of the present invention is directed to a suture. The suture may comprise a cylindrical body. The cylindrical body may comprise a core comprising a plurality of collagen fibers and a layer comprising at least two continuous length collagen fibers. The layer may surround the core and the at least two continuous length collagen fibers are braided together. The layer may further comprise a first layer and the suture may further comprise a second layer that surrounds the core and the first layer. The first layer and the second layer may each comprise at least two continuous length collagen fibers that are braided together.

The plurality of collagen fibers may extend substantially parallel to each other along the longitudinal axis of the core. The plurality of collagen fibers may be braided together.

The suture may further comprise at least one needle attached to at least one end of the cylindrical body.

The core of the suture may comprise 4 collagen fibers and the layer may comprise 16 collagen fibers. The at least two continuous length collagen fibers may be braided at about 5 picks per inch to about 40 picks per inch.

The layer of the suture may comprise a first layer and the suture may further comprise a second layer that surrounds the core and the first layer. The first layer and the second layer may each comprise at least two continuous length collagen fibers that are braided together.

The core of the suture may comprise 12 collagen fibers, the first layer may comprise 16 collagen fibers, and the second layer may comprise 16 collagen fibers. The core of collagen fibers may be braided at about 5 picks per inch, the first layer of collagen fibers may be braided at about 15 picks per inch, and the second layer of collagen fibers may be braided at about 20 picks per inch.

The suture may comprise about 10 collagen fibers to about 60 collagen fibers. The suture may have a diameter of about 0.1 mm to about 1.5 mm. The suture may have a tensile strength of about 10 N to about 50 N. The suture may have a flexural stiffness of about $3\times10^6$ kg/cm$^2$ to about 1 kg/cm$^2$. The collagen fibers may have a length of about 40 cm to about 100 cm. At least a portion of the collagen fibers in the first and/or second layer may have a tensile strength of about 0.5 N to about 5 N, optionally, on average, the collagen fibers in the core, first layer, and/or second layer may have a tensile strength of about 1.5 N to about 3.5 N. The suture may have a length of about 30 cm to about 100 cm.

The suture may comprise a coating applied to the core, the first layer, and/or second layer. The coating may comprise polylactic acid.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF THE INVENTION

Figure 1A:
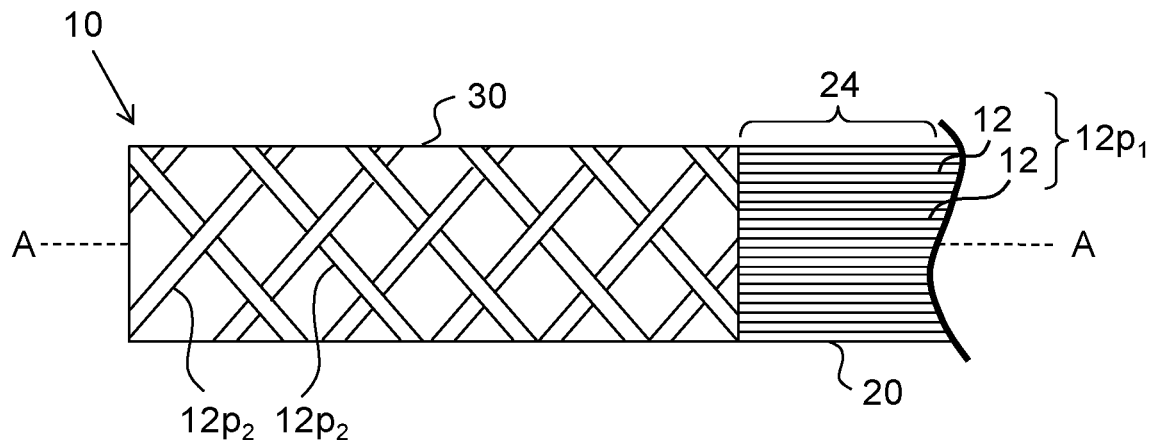
FIG. 1A is an illustrated side view of a construct according to some embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10").

In the figures, certain layers, components or features may be exaggerated for clarity, and broken lines illustrate optional features or operations unless specified otherwise. The terms "FIG." and "FIG." are used interchangeably with the word "Figure" in the application and/or drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

All patents, patent applications and publications referred to herein are incorporated by reference in their entirety for the teachings relevant to the sentence and/or paragraph in which the reference is presented. In case of a conflict in terminology, the present specification is controlling.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "about" when referring to a number and/or value refers to up to +/−20% (e.g., +/−10%, +/−5%, +/−1%) of the number and/or value. A range provided herein includes any other range, number, and/or value therein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the construct in use or operation in addition to the orientation depicted in the figures. For example, if a construct in the figures is inverted, elements described as "under" or "beneath" other elements or features would then be oriented "over" the other elements or features. Thus, the exemplary term "under" can encompass both an orientation of over and under. The construct may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "implantable" and grammatization derivatives thereof means the construct can be inserted, embedded, grafted or otherwise acutely or chronically attached or placed in and/or on a patient. The term "construct" refers to a device and/or material in a final form for use or in a pre-final form.

Embodiments of the present invention are directed to collagen constructs such as, for example, a suture comprising collagen, typically dermal or placental collagen. The collagen may be of any form and from any origin. The collagen may be any of the identified collagen genotypes such as, for example, the interstitial fiber forming collagen types I, II and III, as well as any other substantially fiber forming types of collagen, for example collagen VI. The collagen may be acid soluble collagen or pepsin solubilized and/or soluble collagen. The collagen may be from mammalian cells synthesized in vitro. The collagen may be from molecularly engineered constructs and synthesized by bacterial, yeast or any other molecularly manipulated cell type. In some embodiments, the collagen may be sea cucumber dermis collagen, bovine, caprine, porcine, ovine, human or other suitable donor mammal collagen, marine animal collagen such as chinoderms, molecularly engineered collagen, or gelatin (e.g., in any suitable form including solid, gel, hydrogels, liquids, or foams). In some embodiments, the collagen may be human collagen, including, but not limited to, human placental collagen. In some embodiments, the collagen may be digested with a protease before, optionally prior to, oxidizing and/or polymerizing steps. The collagen may be in the form of microfibrils, fibrils, natural fibers, and/or synthetic fibers.

In some embodiments, the collagen may be solubilized, dissolved or otherwise transferred into an acid solution, for example, acetic acid (e.g., about 0.01 M to about 1 M, typically about 0.5 M), hydrochloric acid (e.g., from about pH 1 to about pH 3, typically about pH 2), or any other suitable acid at appropriate concentration (e.g., about pH 1 to about pH 3, typically about pH 2). Dialysis may optionally be used to neutralize a soluble collagen solution. The collagen may also or alternatively be dissolved in a neutral buffered solution either with or without salts, e.g., phosphate buffer at about pH 7, or phosphate buffered saline at about pH 7. The phosphate buffer may have a sodium phosphate concentration from about 0.01 M to 0.5 M, but optionally from about 0.02 M to about 0.1 M. Further exemplary buffers include, but not limited to, for example, sodium acetate, HEPES, and MOPS. The collagen may be present in a solution (e.g., a buffer) in an amount of about 0.1% to about 10%, optionally about 0.1% to about 5% (e.g., about 0.1%, 0.2%, 0.3%, 0.4%, 1%, 2%, 4%) by weight per volume of the solution before fibrillogenesis and fiber formation. In a dried collagen fiber, collagen may be present in an amount of about 50% to about 100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 nm to about 50 nm in diameter. Fibrils are about 50 nm to about 50 μm in diameter. Natural fibers are above 50 μm in diameter. A "synthetic fiber" refers to any fiber-like material that has been formed and/or chemically and/or physically created or altered from its naturally-occurring state. For example, an extruded collagen fiber of fibrils formed from a digested tendon is a synthetic collagen fiber but a tendon fiber newly harvested from a mammal is a natural collagen fiber.

In some embodiments, other materials may be used with a collagen fiber to form the construct. For example, non-cytotoxic (and typically non-inflammatory) polymers including thermoplastic materials and/or polymers based on monomers such as acrylates, e.g., polymers which are prepared by copolymerizing two or more of the monomers such as alkyl acrylate monomers (e.g., methyl acrylate, ethyl acrylate, butyl acrylate or octyl acrylate); alkyl methacrylate monomers (e.g., methyl methacrylate or ethyl methacrylate); acrylic acid or methacrylic acid; vinyl cyanide monomers (e.g., acrylonitrile or methacrylonitrile); aromatic vinyl monomers (e.g., styrene or a-methylstyrene); and vinyl halide monomers (e.g., vinyl chloride or vinyl bromide). In addition to the monomers, cross-linking agents such as divinylbenzene, monoethylene glycol dimethacrylate and polyethylene glycol dimethacrylate may be used alone or as a mixture of two or more. In some embodiments, alkyl methacrylate monomers and aromatic vinyl monomers may be used and/or polymerized, with an alkyl acrylate monomer and an alkyl methacrylate monomer. Combinations of an alkyl acrylate monomer and an aromatic vinyl monomer for a biocompatible thermoplastic material may be useful, including, but not limited to, a combination of butyl acrylate and methyl methacrylate and a combination of butyl acrylate and styrene.

In some embodiments, the collagen fibers can comprise glutaraldehyde cross-linked collagen fibers and/or NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, and then extruded into a synthetic fiber. Properly processed NDGA polymerized fibers are biocompatible. After the polymerization process, the collagen fibers can be washed in ethanol and phosphate buffered saline to remove cytotoxins due to leachable reaction products.

The collagen fibers and/or polymeric and/or thermoplastic materials may include other non-collagenous components or biocompatible materials, such as, e.g., therapeutic agents. The term "therapeutic agent" means a biologically active agent, drug and/or compound used for generating a clinical therapeutic effect. Examples of such therapeutic agents include, but are not limited to, particulates, hydroxyapatite and other mineral phases, and/or drugs that facilitate tissue growth, inhibit inflammation, treat infections, reduce pain, thin blood, inhibit coagulation, blockage, plaque build-up or provide other desired therapies or effects, including, in some embodiments, heparin and/or growth hormones. See, e.g., U.S. Pat. No. 6,821,530, incorporated herein by reference above. For example, the fibers and/or constructs formed from the same, can include carbon nano-tubes, zinc nanowires, nano-crystalline diamond, or other nano-scale particulates, and larger crystalline and non-crystalline particulates such as calcium phosphate, calcium sulfate, apatite minerals. For example, the fibers and/or constructs may contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or constructs may contain cells, such as, but not limited to, engineered cells, stem cells, and the like. Combinations of the above or other materials may be embedded, coated and/or otherwise directly or indirectly attached to a collagen fiber(s) and/or construct of the present invention (such as in a liquid polymeric material used to apply a film).

A collagen fiber of the present invention may be formed from a collagen gel that includes collagen fiber, fibrils and/or microfibrils, typically dermal or placental collagen, that has been acid or pepsin solubilized (e.g., soluble collagen) and processed to maintain the collagen in its molecular form. The collagen concentration of the soluble collagen and/or resulting soluble collagen gel may be about 0.1% to about 4% weight per volume. The soluble collagen gel may be formed to be in a cylindrical shape of a defined length and diameter, typically with a diameter of about 0.1 cm to 1 cm, and a length of about 5 cm to about 100 m, more typically a length of about 10 m to about 50 m, which is subsequently dried to form a collagen fiber.

The collagen fiber and/or collagen gel may be produced in batch or continuous-type systems, including wet gel collagen extrusion systems, which produce cylindrical lengths of gel that may be allowed to substantially dry (actively or passively) to obtain a suitable length of fiber. Examples of some collagen fiber production processes that may generate soluble collagen in suitable lengths are described in U.S. Pat. No. 6,565,960 and pending U.S. Patent Application Publication No. 2008/0188933A1, the contents of each of which are hereby incorporated by reference.

The collagen fiber(s) may be spooled (e.g., held wound on a spool) for supplying to an automated or semi-automated winder and/or braider to form a construct. The spooled fiber(s) may be in a dry state or may be in a hydrated or partially hydrated state. The collagen fiber(s) may be formed with a relatively thin diameter, such as, for example, from about 0.05 mm to about 0.2 mm (average) (dry or wet). In some embodiments, a collagen fiber may have a dry diameter of about 0.08 mm (average) and/or a wet diameter of about 0.13 mm (average). At least one collagen fiber on the spool for the winding and/or braiding may be formed as a single continuous length of about 1 m to about 100 m or may be formed with multiple fibers joined end-to-end to form a desired length for the winding and/or braiding.

A component of a construct of the present invention (e.g., a collagen fiber) and/or a construct of the present invention (e.g., a medical construct or suture) may be dry or hydrated (e.g., partially or fully hydrated). The term "dry" as used herein means the component and/or construct has a water content of less than about 5% by weight of the respective component and/or construct. The term "partially hydrated" as used herein means that the component and/or construct has a water content that is less than about 100% of the water content at full hydration. In some embodiments, full hydration is measured ex vivo after 24 hours in a saline bath at ambient conditions and compared to the component and/or construct at a dry weight. In some embodiments, the component and/or construct may have a water content of less than about 25% by weight of the respective component and/or construct, such as less than about 15% by weight of the respective component and/or construct.

In some embodiments of the present invention, a construct may be made from at least one collagen fiber and a non-cytotoxic polymeric material such as, e.g., polyacrylate emulsions and/or other thermoplastic materials, and the collagen fiber(s) may be either cross-linked or uncrosslinked. The polymeric material may be applied in a liquid state to the collagen fiber. In some embodiments, the liquid polymeric material may be a microemulsion. The polymeric material may further include one or more additives including, but not limited to, surfactants, antioxidants, solvents, polymerization inhibitors, chain transfer agents, fillers, thickening agents, flow agents, polymerization initiators and accelerators, lubricants, air release agents, wetting agents, UV stabilizers, compatibilizers, fire retardants, urethane reaction catalysts, moisture scavengers, shrink-reducing additives, and/or one or more therapeutic agent(s).

A construct of the present invention may comprise an array of collagen fibers, and the array may braided, woven, twisted, and/or the like. A construct may comprise various patterns of fiber(s) in various orientations and/or fiber densities (dense to sparse and/or tight to loose geometries) to meet the desired mechanical properties for the target use.

Embodiments of the present invention are directed to constructs, such as, for example, medical sutures. A construct of the present invention may comprise one or more layers or pluralities of collagen fibers (e.g., 1, 2, 3, 4, 5 or more). A layer of the construct may comprise a plurality of collagen fibers which may include one or more (e.g., 1, 5, 10, 20, etc.) collagen fibers and may optionally extend substantially parallel to each other along a longitudinal axis of the construct and/or may be braided together. The collagen fibers may be braided and/or woven in a variety of repeating and/or alternating braid patterns. For example, the braid pattern may comprise at least one collagen fiber in a layer passing over one or more collagen fibers and under one or more different collagen fibers and repeating this pattern for a given length. A needle may be attached to at least one end of the construct.

Figure 1B:
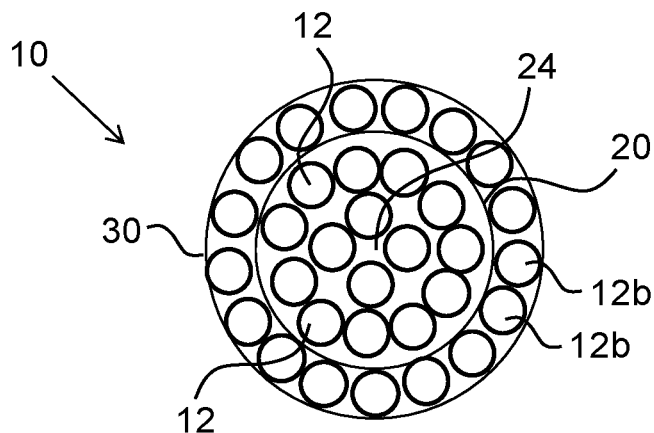
FIG. 1B is an illustrated end view of the construct of FIG. 1A.

Referring now to the figures, FIGS. 1A and 1B illustrate a construct 10 (e.g., a medical construct or suture) according to some embodiments of the present invention. A construct 10 may comprise a first layer 20 and a second layer 30. The first layer 20 may comprise a first plurality of collagen fibers $12p_1$ (e.g., synthetic collagen fibers) forming a core 24 of the construct 10. The second layer 30 may comprise a second plurality of collagen fibers $12p_2$. The second layer 30 may surround the first layer 20 or core 24 of the construct 10.

Figure 2:
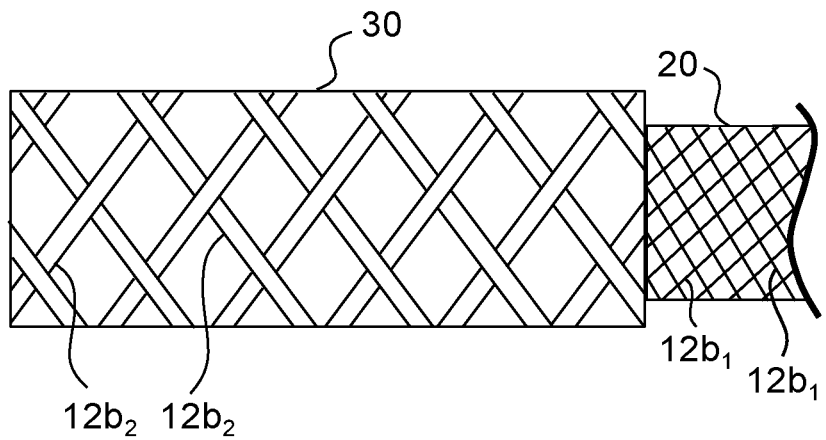
FIG. 2 is an illustrated side view of a construct showing the core being comprised of braided collagen fibers.

In some embodiments, each collagen fiber 12 of the first plurality of collagen fibers $12p_1$ may extend substantially parallel to each other along a longitudinal axis (A) of the first layer 20 and/or core 24 of the construct 10. The term "substantially" with respect to collagen fibers 12 arranged parallel to each other means up to +/−15% variation (e.g., +/−1%, +/−5%, +/−10%) between adjacent longitudinally extending lengths of the collagen fibers 12. In some embodiments, the first plurality of collagen fibers $12p_1$ may be braided together forming a first plurality of braided collagen fibers $12b_1$ (FIG. 2). In some embodiments, the second layer 30 of the construct 10 may comprise a second plurality of braided collagen fibers $12b_2$.

A construct 10 may comprise about 10, 15, 20, 25, or 30 collagen fibers 12 to about 35, 40, 45, 50, 55, or 60 collagen fibers 12. A layer (e.g., a first layer 20 and/or second layer 30) of the construct 10 may comprise about 1, 5, or 10 collagen fibers 12 to about 15, 20, 25, or 30 collagen fibers 12. For example, in some embodiments, the first layer 20 of the construct 10 may comprise 4 collagen fibers 12 and the second layer 30 of the construct 10 may comprise 16 collagen fibers 12.

A collagen fiber 12 present in a layer (e.g., a first layer 20 and/or second layer 30) of the construct 10 may have a length of about 40, 45, 50, 55, 60, or 65 cm to about 70, 75, 80, 85, 90, 95, or 100 cm. A construct 10 may have an overall length of about 30, 35, 40, 45, 50, 55, 60, or 65 cm to about 70, 75, 80, 85, 90, 95, or 100 cm, and may be cut to a desired size during use.

Figure 3:
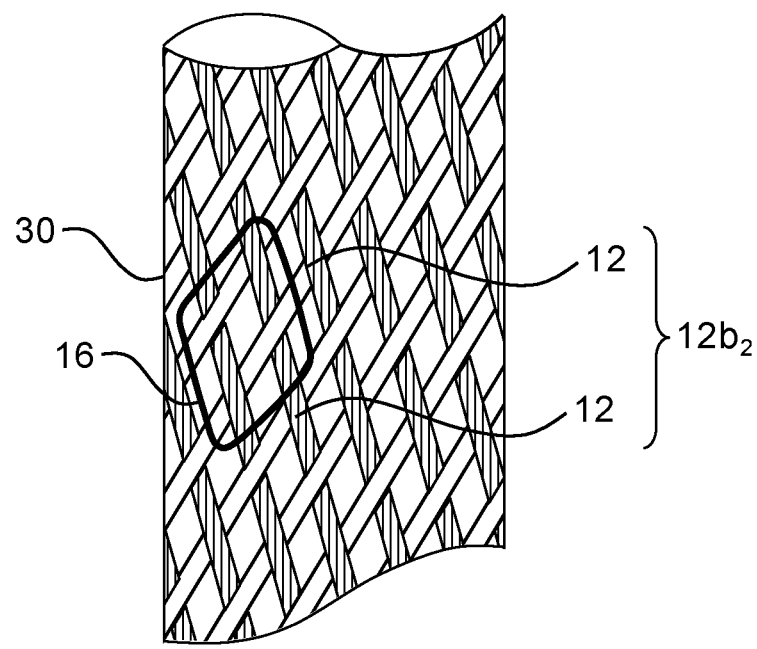
FIG. 3 is an illustrated example braid pattern according to some embodiments of the present invention.

There are a variety of different braid patterns in which a plurality of collagen fibers (e.g., a first plurality and/or second plurality of braided collagen fibers $12b_1$, $12b_2$) may be braided. A first plurality of collagen fibers may be braided to form a first plurality of braided collagen fibers $12b_1$ and the first plurality of braided collagen fibers $12b_1$ may have a braid pattern where each collagen fiber of the plurality of collagen fibers pass over one or more collagen fibers 12 (e.g., 1, 2, 3, 4, 5 or more) and then under one or more collagen fibers 12 (e.g., 1, 2, 3, 4, 5 or more), which is repeated. For example, in some embodiments, like shown in FIG. 3, the collagen fibers in the first plurality of braided collagen fibers $12b_1$ (and/or second plurality of braided collagen fibers $12b_2$) may be braided in a repeating braid pattern in which each collagen fiber 12 of the plurality passes over one collagen fiber 12 and then under one collagen fiber 12 and this pattern is repeated.

In some embodiments, collagen fibers 12 in a layer (e.g., the first plurality of braided collagen fibers $12b_1$ and/or second plurality of braided collagen fibers $12b_2$) may be braided in a repeating braid pattern in which each collagen fiber 12 of the plurality passes over two collagen fibers 12 and then under two collagen fibers 12 and this pattern is repeated.

Figure 4:
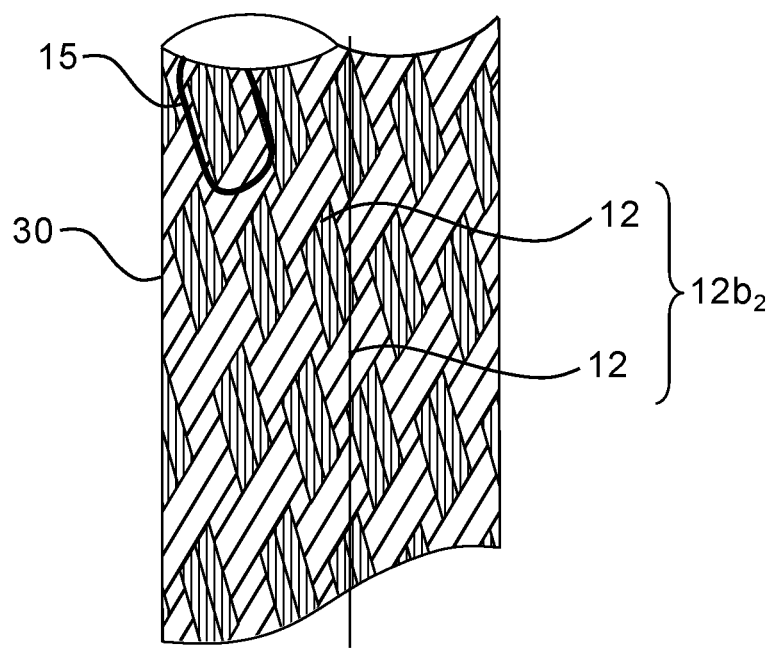
FIG. 4 is another illustrated example braid pattern according to some embodiments of the present invention.

A layer (e.g., the first plurality of braided collagen fibers $12b_1$ and/or second plurality of braided collagen fibers $12b_2$) may comprise one or more paired collagen fibers 12. A first plurality and/or second plurality of braided collagen fibers $12b_1$, $12b_2$ may comprise paired collagen fibers 12. Paired collagen fibers 12 are two collagen fibers 12 that reside side-by-side and may be in at least partial contact with each other. In some embodiments, paired collagen fibers 12 may follow the same braid pattern. In some embodiments, paired collagen fibers 12 may follow a different pattern (e.g., may alternate). For example, as shown in FIG. 4, paired collagen fibers 15 are arranged in a repeating braid pattern in which the pair of collagen fibers 15 passes over another pair of collagen fibers 12, then under another pair of collagen fibers 12 and this pattern is repeated.

A layer (e.g., the first plurality and/or second plurality of braided collagen fibers $12b_1$, $12b_2$) may comprise non-paired collagen fibers arranged in an alternating braid pattern. Non-paired collagen fibers refer to single collagen fibers that are not paired but are immediately adjacent to another collagen fiber. Non-paired collagen fibers in the first plurality of braided collagen fibers $12b_1$ and/or second plurality of braided collagen fibers $12b_2$ may be arranged in an alternating braid pattern from each other. For example, as shown in, in some embodiments, a collagen fiber 12 passes under a first collagen fiber 12 and over a second collagen fiber 12, and an adjacent collagen fiber 12' passes over the first collagen fiber 12 and under the second collagen fiber 12. In this manner, the non-paired collagen fibers 12 are arranged in an alternating braid pattern (see, e.g., adjacent collagen fibers 16 in FIG. 3).

Figures 5, 6:
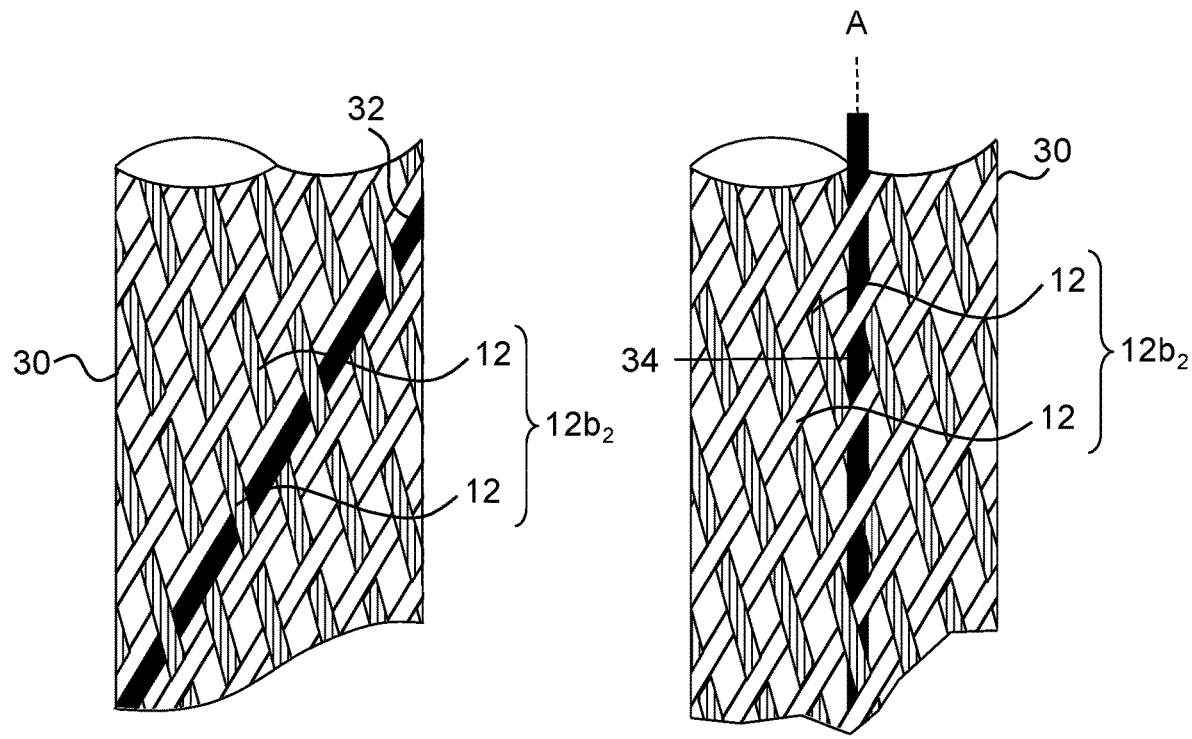
FIG. 5 is an illustration showing the use of a chase fiber according to some embodiments of the present invention.
FIG. 6 is an illustration showing the use of a tri-axe fiber according to some embodiments of the present invention.
Figure 7:
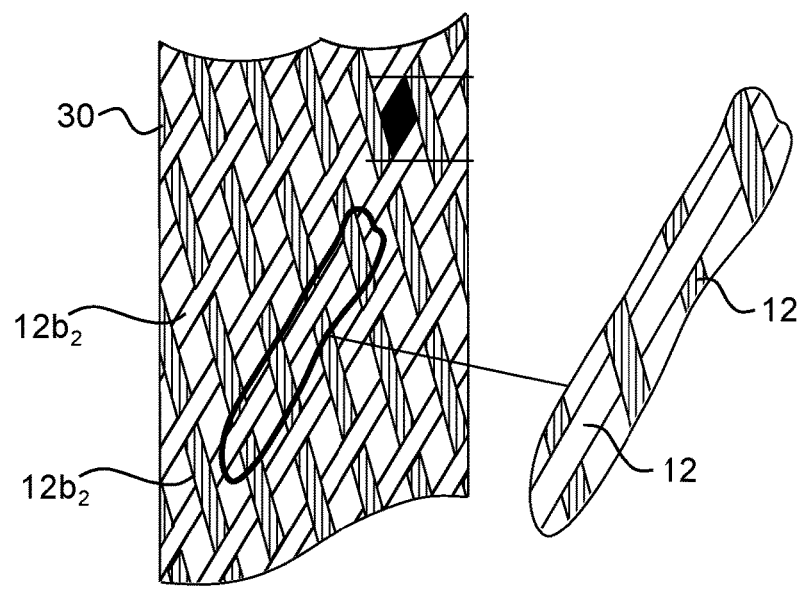
FIG. 7 is another illustrated example braid pattern according to some embodiments of the present invention.

As shown in FIG. 5, in some embodiments, a plurality of collagen fibers of a construct of the present invention (e.g., a first plurality of braided collagen fibers $12b_1$ and/or second plurality of braided collagen fibers $12b_2$) may comprise at least one chase fiber 32. A chase fiber 32 is an additional fiber and/or wire that is braided next to a collagen fiber 12 and may provide additional support to the construct 10. The chase fiber 32 may be a biocompatible yarn or fiber, or one or more collagen fiber(s). "Biocompatible" as used herein means compatible with living tissue and/or a living system by not being toxic, injurious, and/or not causing an immunological rejection.

In some embodiments, as shown in FIG. 6, a plurality of collagen fibers of a construct of the present invention (e.g., a first plurality of braided collagen fibers $12b_1$ and/or second plurality of braided collagen fibers $12b_2$) may comprise at least one tri-axe fiber 34. A tri-axe fiber 34 is an additional fiber and/or wire that is routed straight within the braid pattern along the longitudinal axis (A) of the construct 10. The tri-axe fiber 34 may provide additional support to the construct 10. Like the chase fiber 32, the tri-axe fiber 34 may be a biocompatible yarn or fiber, or one or more collagen fiber(s).

Figure 8:
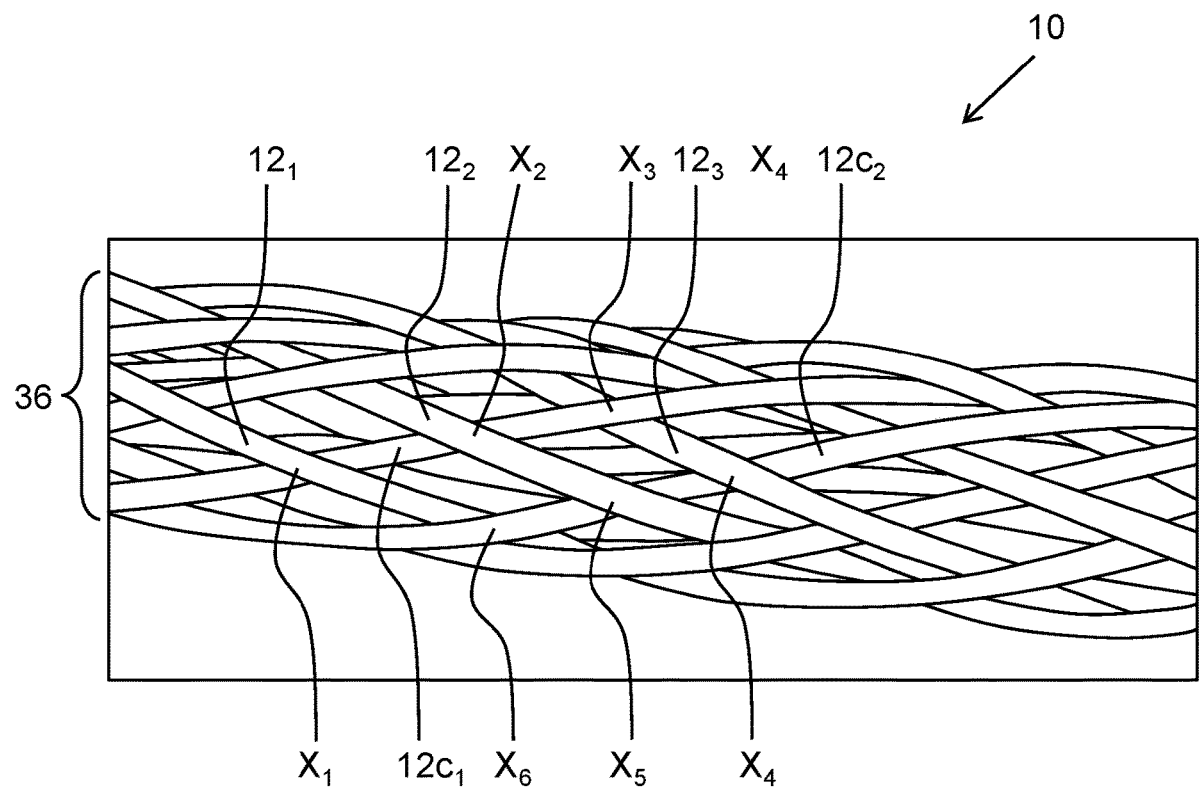
FIG. 8 is a digital image of an example construct of according to some embodiments of the present invention magnified at 10X.

FIG. 8 is a digital image of a construct 10 according to some embodiments of the present invention shown at a magnification of 10X. A plurality of collagen fibers 12 of a construct of the present invention (e.g., a first plurality of braided collagen fibers $12b_1$ and/or second plurality of braided collagen fibers $12b_2$) may comprise a first, second, and third collagen fiber $12_1$, $12_2$, $12_3$ with the second collagen fiber $12_2$ being in between the first collagen fiber $12_1$ and third collagen fiber $12_3$. The first, second, and third collagen fibers $12_1$, $12_2$, $12_3$ may be braided together to form a braid 36. In some embodiments, the first, second, and/or third collagen fibers $12_1$, $12_2$, $12_3$ may be paired collagen fibers 12 (FIG. 8). As shown in FIG. 8, each of the paired collagen fibers 12 follow the same braid pattern.

Still referring to FIG. 8, in some embodiments, the braid 36 may comprise a portion in which the first collagen fiber $12_1$ and second collagen fiber $12_2$, each separately form a pick $X_1$, $X_2$ (i.e., crossing point or intersection) over a first crossing collagen fiber $12c_1$ and the third collagen fiber $12_3$ passes under the first crossing collagen fiber $12c_1$ forming another pick $X_3$. The braid 36 may also comprise a portion in which the second collagen fiber $12_2$ and third collagen fiber $12_3$ each separately form a pick $X_4$, $X_5$ over a second crossing collagen fiber $12c_2$, and the first collagen fiber $12_1$ forms a pick $X_6$ passing under the second crossing collagen fiber $12c_2$. As such, the first and third collagen fibers $12_1$, $12_3$ are arranged in an alternating braid pattern and the second collagen fiber $12_2$ is offset by one.

The construct 10 shown in FIG. 8 is braided in a repeating braid pattern in which the pattern for each collagen fiber $12_1$, $12_2$, $12_3$ of the plurality is such that each collagen fiber $12_1$, $12_2$, $12_3$ passes over two crossing collagen fibers $12c$ and then under two crossing collagen fibers $12c$ and this pattern is repeated. In some embodiments, the first and second collagen fibers $12_1$, $12_2$ and/or the second and third collagen fibers $12_2$, $12_3$ have a braid pattern in which picks X are formed under the same crossing collagen fiber $12c$ or an alternate crossing collagen fiber $12c$.

One or more layers of a construct may have the same or different number of picks per inch compared to another layer of the construct. For example, in some embodiments, the first plurality of braided collagen fibers $12b_1$ may have a greater number of picks per inch than the second plurality of braided collagen fibers $12b_2$ or visa-versa. As used herein, "picks per inch" or "PPI" refers to the number of collagen fiber 12 crossing points per inch along the longitudinal axis (A) of the braid 36 or construct 10. The number of picks per inch is one way to describe the tightness of a braid 36. For example, the higher the number of picks per inch, the tighter or more closely compact the braid 36. A plurality of collagen fibers 12 of a construct of the present invention (e.g., a first plurality of braided collagen fibers $12b_1$ and/or second plurality of braided collagen fibers $12b_2$) may be braided at about 5, 10, 15, or 20 PPI to about 25, 30, 35, or 40 PPI.

Figure 9A:
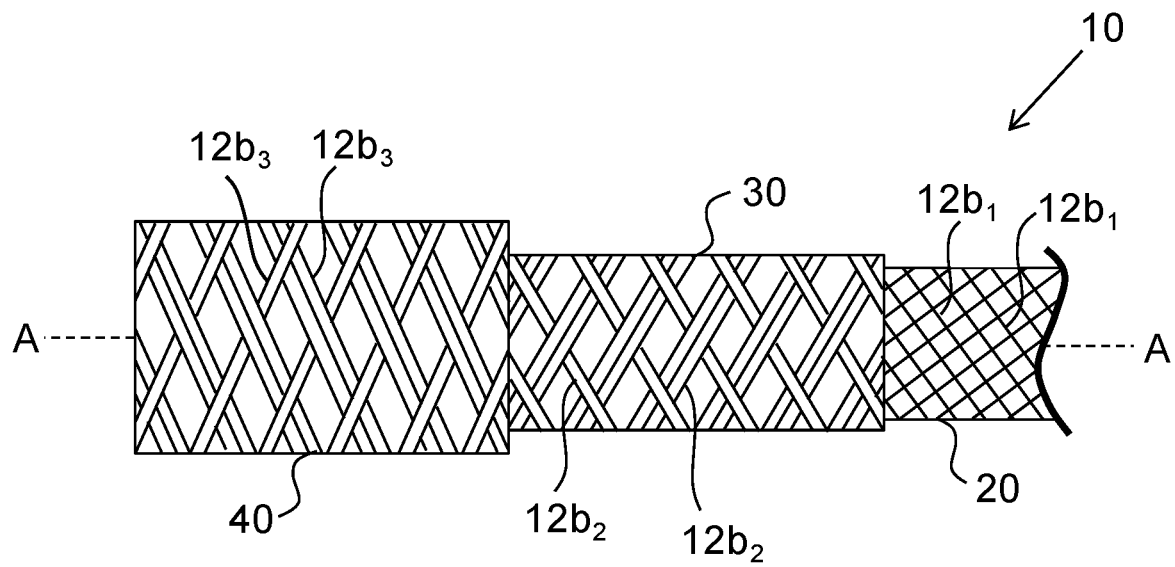
FIG. 9A is an illustrated side view of a construct according to further embodiments of the present invention.
Figure 9B:
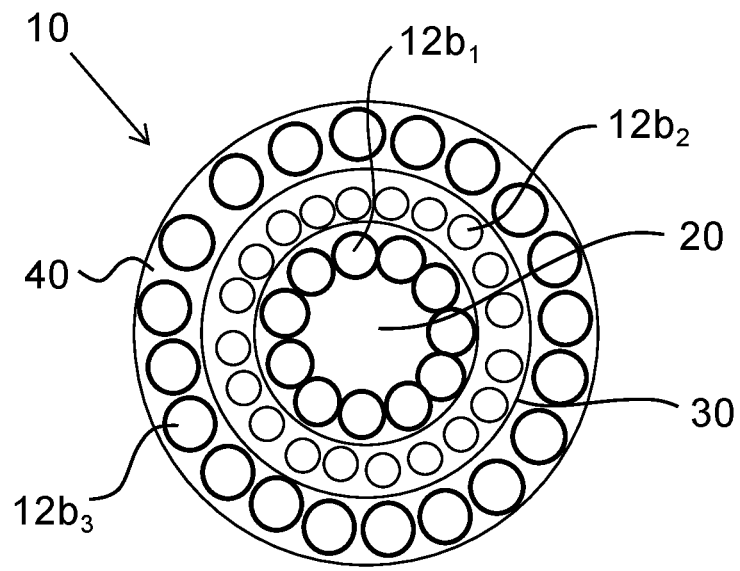
FIG. 9B is an illustrated end view of the construct of FIG. 9A.

Referring now to FIGS. 9A and 9B, in some embodiments, a construct 10 of the present invention may further comprise a third layer 40. The third layer 40 may comprise a third plurality of braided collagen fibers $12b_3$. The third layer 40 may surround the first layer 20 and the second layer 30. A layer of the construct 10 (e.g., a first layer 20, second layer 30, and/or third layer 40) of the may comprise about 1, 5, or 10 collagen fibers 12 to about 15, 20, or 25 collagen fibers 12. For example, in some embodiments, the first layer 20 of the construct 10 may comprise 12 collagen fibers 12, the second layer 30 may comprise 16 collagen fibers 12, and the third layer 40 may comprise 16 collagen fibers 12.

In some embodiments, a third plurality of braided collagen fibers $12b_3$ may optionally have a number of picks per inch that is greater than the first plurality of braided collagen fibers $12b_1$ and/or the second plurality of braided collagen fibers $12b_2$. For example, in some embodiments, the first layer 20 of collagen fibers 12 may be braided at about 5 PPI, the second layer 30 of collagen fibers 12 may be braided at about 15 PPI, and the third layer 40 of collagen fibers 12 may be braided at about 20 PPI.

One or more of the collagen fibers 12 in a plurality of collagen fibers 12 of a construct of the present invention (e.g., a first plurality, second plurality, and/or third plurality of braided collagen fibers $12b_1$, $12b_2$, $12b_3$) may each have a tensile strength of about 0.5, 0.75, 1, 1.5, 2, or 2.5 N to about 3, 3.5, 4, 4.5, or 5 N. For example, in some embodiments, the collagen fibers 12 in the first, second, and/or third plurality $12b_1$, $12b_2$, $12b_3$ may have a tensile strength, on average, of about 1.5, 1.75, 2, 2.25, or 2.5 N to about 2.75, 3, 3.25, or 3.5 N. A construct 10 of the present invention may have an overall tensile strength of about 10, 15, 20, or 25 N to about 30, 35, 40, 45, or 50 N.

Like described above (see, e.g., FIG. 3 and FIG. 4), there are a variety of different braid patterns in which a plurality (e.g., a first, second and/or third plurality) of braided collagen fibers $12b_1$, $12b_2$, $12b_3$ may be braided in a construct of the present invention. The first plurality, second plurality, and/or third plurality of braided collagen fibers $12b_1$, $12b_2$, $12b_3$ may be arranged in a repeating and/or alternating braid pattern. For example, in some embodiments, the first plurality, second plurality, and/or third plurality of braided collagen fibers $12b_1$, $12b_2$, $12b_3$ may be braided in a repeating braid pattern in which each collagen fiber 12 of the plurality passes over one collagen fiber 12 and then under one collagen fiber 12, which is repeated. In some embodiments, the first plurality, second plurality, and/or third plurality of braided collagen fibers $12b_1$, $12b_2$, $12b_3$ are braided in a repeating braid pattern in which each collagen fiber 12 of the plurality passes over two collagen fibers 12 and then under two collagen fibers 12, which is repeated. In some embodiments, each collagen fiber in the plurality of braided collagen fibers $12b_1$, $12b_2$, $12b_3$ may pass over one collagen fiber 12 and then under two collagen fibers 12. In some embodiments, each collagen fiber in the plurality of braided collagen fibers $12b_1$, $12b_2$, $12b_3$ may pass over two collagen fibers 12, then under one collagen fiber 12, or may pass under three collagen fibers 12, then over one collagen fiber 12, etc., each of which is repeated.

In some embodiments, the first plurality, second plurality, and/or third plurality of braided collagen fibers $12b_1$, $12b_2$, $12b_3$ of the construct 10 may comprise paired collagen fibers 12. In some embodiments, the first plurality, second plurality, and/or third plurality of braided collagen fibers $12b_1$, $12b_2$, $12b_3$ of the construct 10 may comprise non-paired collagen fibers 12 that may be arranged in an alternating braid pattern.

Similar to embodiments described above (see, e.g., FIG. 5 and FIG. 6), in some embodiments, the first, second, and/or third plurality of braided collagen fibers $12b_1$, $12b_2$, $12b_3$ may comprise at least one chase fiber 32 and/or may comprise at least one tri-axe fiber 34.

Figure 10A:
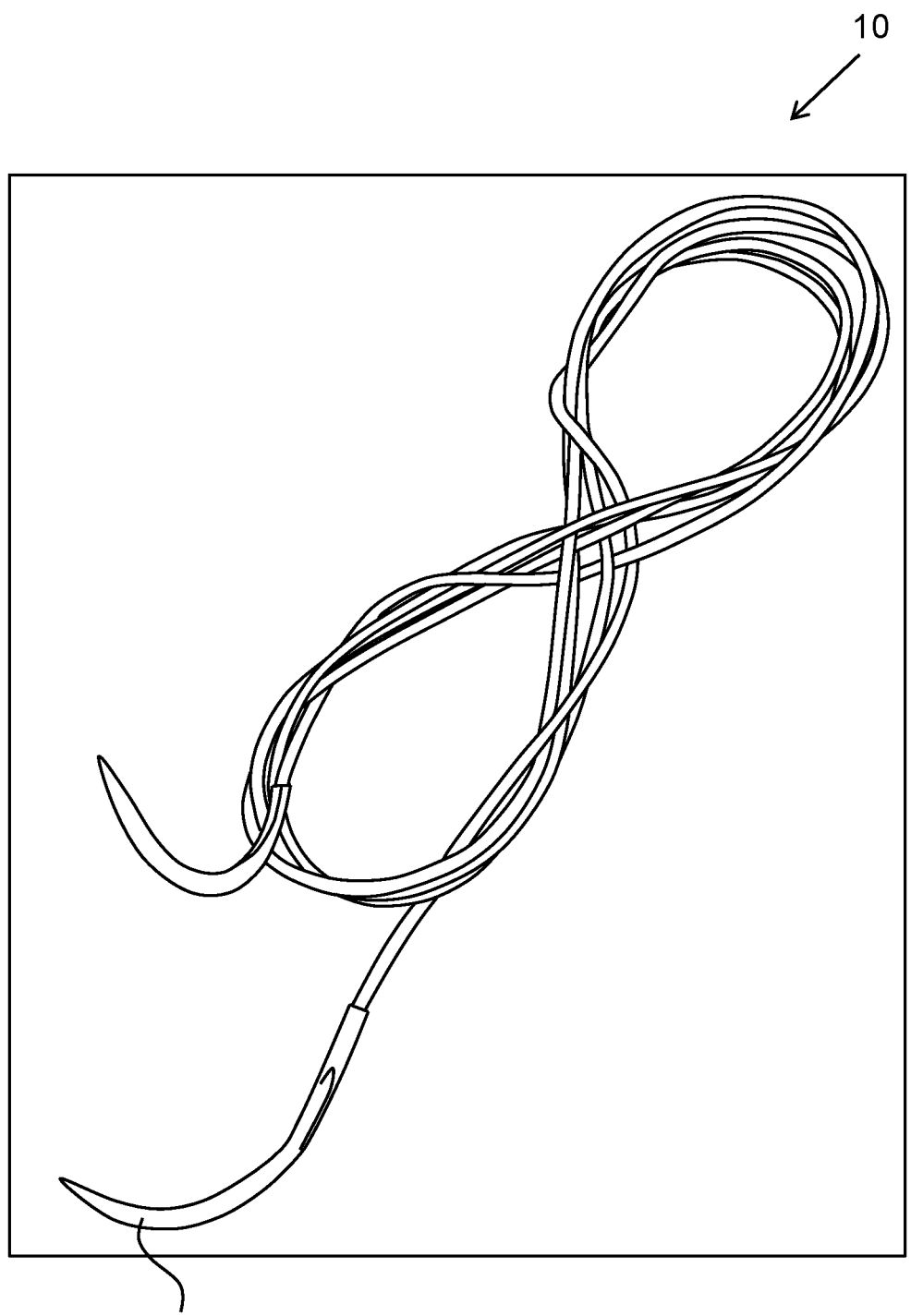
FIG. 10A is a digital image of an example construct according to some embodiments of the present invention.
Figure 10B:
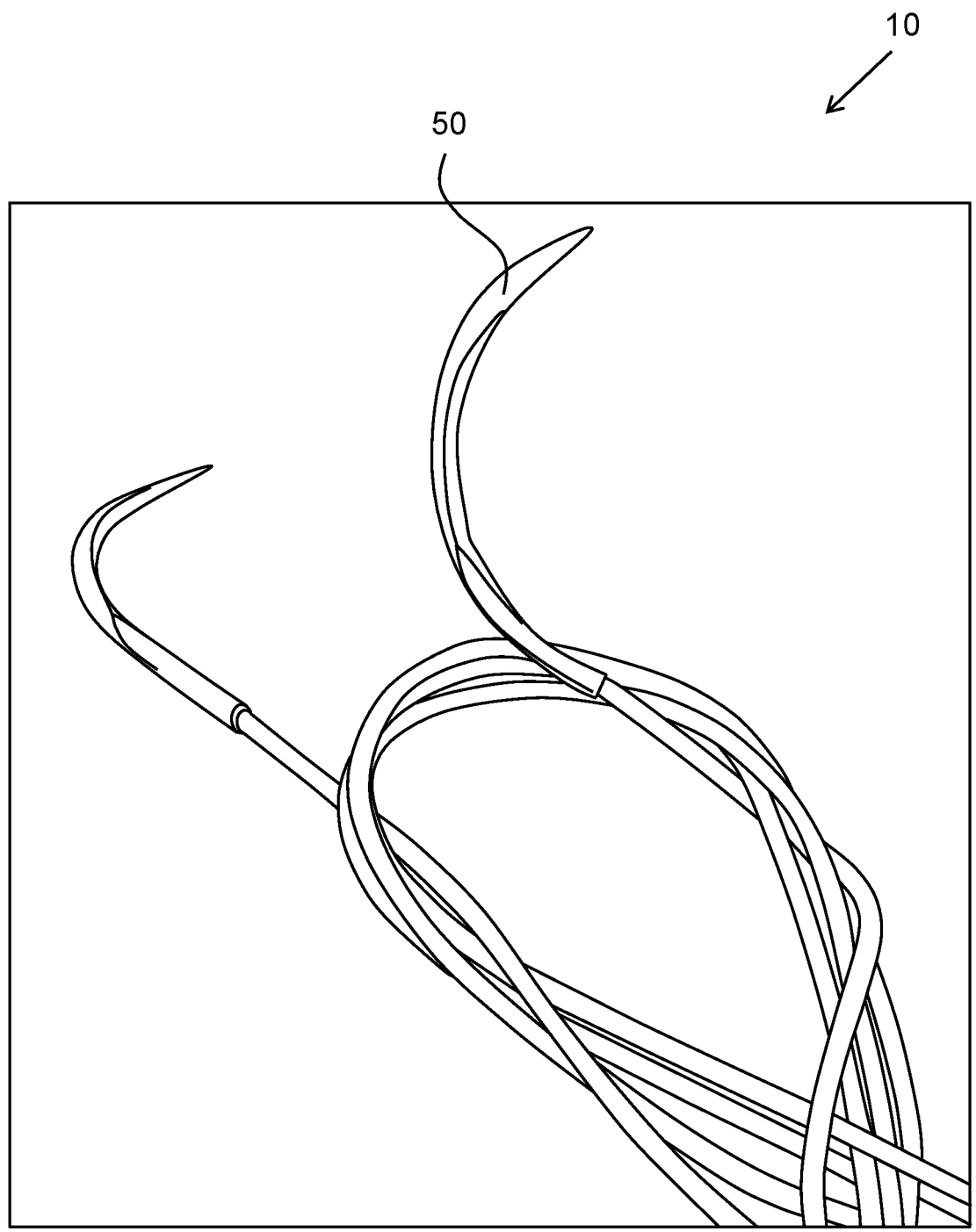
FIG. 10B is an enlarged digital image of the construct of FIG. 10A.

In some embodiments, the construct 10 may further comprise a coating. The coating may be applied to one or more collagen fibers 12 and/or layers 20, 30, 40 or the construct 10 (e.g., a first plurality, second plurality, and/or third plurality of braided collagen fibers $12b_1$, $12b_2$, $12b_3$). In some embodiments, the coating may comprise polylactic acid (PLA). In some embodiments, a construct 10 may further comprise a needle 50 attached to at least one end of the construct 10 (see, e.g., FIGS. 10A and 10B).

The stiffness of a construct 10 may determine its performance in terms of handling characteristics, for example, knot strength and/or security, particularly in closing wounds with small loops. For example, a stiff construct 10 may be difficult to tie into a knot. One way to quantitatively evaluate the stiffness of a construct 10 is by bending a construct having a fixed length to a predetermined angle. The force required to bend the construct to this predetermined angle may be recorded in Taber Stiffness units and used to calculate the flexural stiffness, E, of the construct 10, which can be done according to the formula given in ASTM D747-50:

$$E=0.006832\times\{1/(W\times d^3\times\theta)\}\times T$$

where:

E=stiffness in flexure in pounds/inch$^2$ (converted to kg/cm$^2$ by multiplying by 0.0703)

W=width of construct in inches (the diameter of the construct)

d=thickness of the construct in inches (diameter of collagen fiber)

θ=deflection of construct converted to radian (i.e., 7.5=0.1309 radian)

T=measurement in Taber Stiffness units

A construct 10 according to some embodiments of the present invention may have a flexural stiffness of about $1\times10^6$, $2\times10^6$, or $3\times10^6$ kg/cm$^2$ to about 0.5, 0.75, or 1 kg/cm$^2$. A construct 10 may have a diameter of about 0.1, 0.25, 0.5, or 0.75 mm to about 1, 1.25, or 1.5 mm.

Figure 11A:
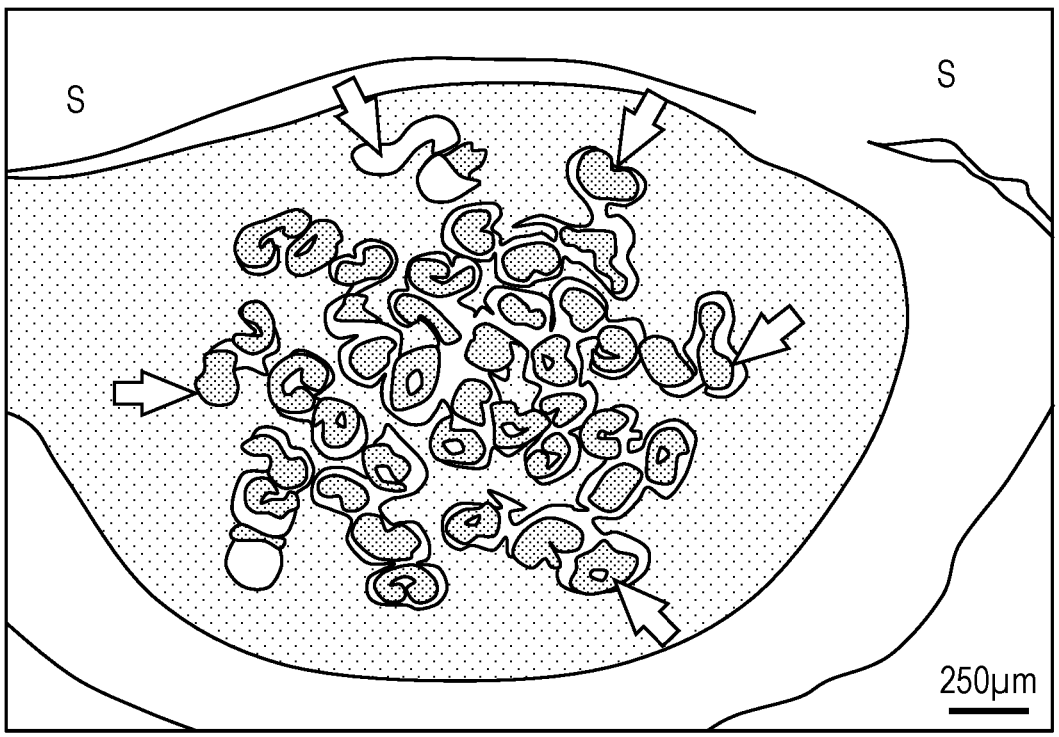
FIGS. 11A and 11B are histology images showing cell integration into the braided collagen fibers of a construct according to some embodiments of the present invention.
Figure 11B:
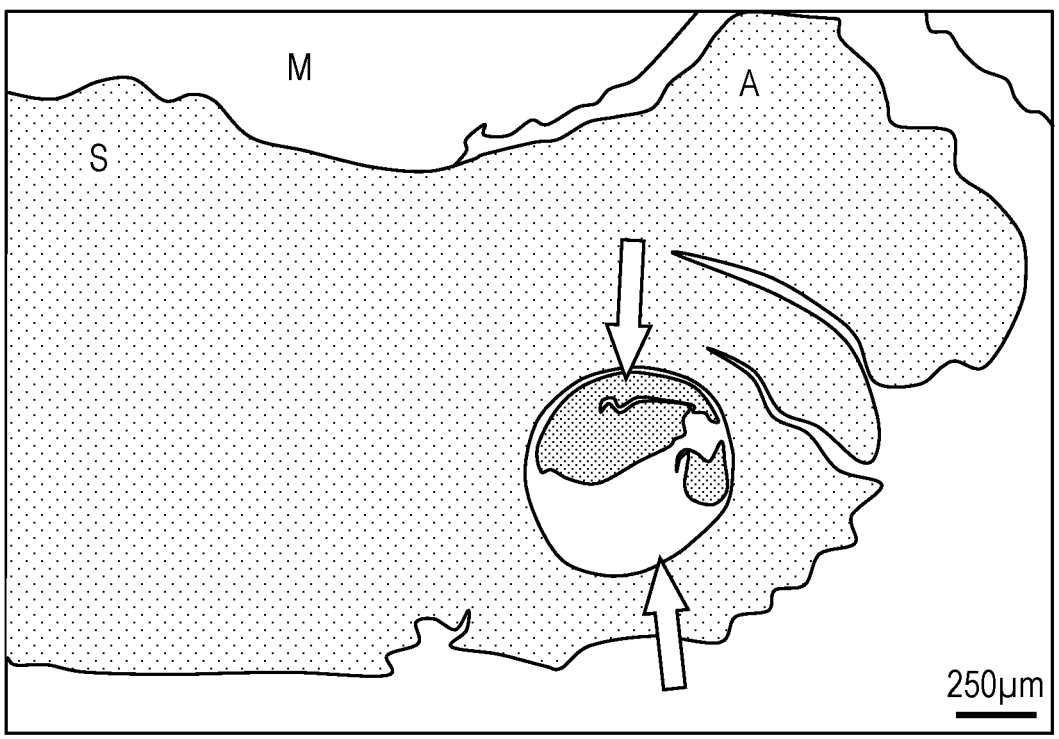

In some embodiments, as shown in FIGS. 11A and 11B, when a construct 10 is used in and/or on a subject and/or implanted in a subject, cell ingrowth may occur within and/or between one or more collagen fibers 12 and/or layers 20, 30, 40 of the construct 10 (e.g., a first plurality, second plurality, and/or third plurality of braided collagen fibers $12b_1$, $12b_2$, $12b_3$). In some embodiments, cells may infiltrate a braid 36 and/or attach to or surround a collagen fiber 12 in a construct 10 (see, e.g., Example 1). In some embodiments, one or more cell(s) may be attached to a collagen fiber 12 and/or layer 20, 30, 40 of a construct 10 such that at least about 5%, 10%, 15%, 20%, 25%, 30%, 35%, 40%, 45%, 50%, 55%, 60%, 65%, 70%, 75%, 80%, 85%, 90%, 95% or 100% of the outer surface of the construct 10 comprises one or more attached cell(s), optionally within 1, 2, 3, 4, 5, 6, 7, 8, 9, 10, 11, 12 or 13 days and/or week(s). In some embodiments, one or more collagen fibers 12 may be within or between two or more collagen fibers 12 of a construct 10 such that at least 5%, 10%, 15%, 20%, 25%, 30%, 35%, 40%, 45%, 50%, 55%, 60%, 65%, 70%, 75%, 80%, 85%, 90%, 95% or 100% of the inner area of the construct 10 comprises one or more attached cell(s), optionally within 1, 2, 3, 4, 5, 6, 7, 8, 9, 10, 11, 12 or 13 days and/or week(s).

Still referring to FIGS. 11A and 11B, the gray or black color kidney bean shapes are cross-sections of a construct 10 including collagen fibers 12. The arrowheads in FIG. 11A show implanted material within subcutaneous tissue. The arrows in FIG. 11B show implanted material within subcutaneous tissue. This cell ingrowth may occur between Day 0 (i.e., the day of implantation) and Day 7, as measured ex vivo using Hematoxylin and Eosin (H&E) staining of resected and fixed constructs 10.

Methods of manufacturing a construct 10 are also provided. In some embodiments, a method may comprise providing a first plurality of collagen fibers 12 and braiding a second plurality of collagen fibers $12b_2$ around the first plurality of collagen fibers 12, thereby forming a construct 10.

In some embodiments, each collagen fiber 12 of the first plurality of collagen fibers 12 may extend substantially parallel to each other along the longitudinal axis (A) of the construct 10. In some embodiments, the first plurality of collagen fibers $12p$ may be braided together. A plurality of collagen fibers (e.g., a first plurality and/or second plurality of braided collagen fibers $12b_1$, $12b_2$) may be braided at about 5, 10, 15, or 20 PPI to about 25, 30, 35 or 40 PPI.

A method may further comprise braiding a third plurality of collagen fibers $12b_3$ around the second plurality of braided collagen fibers $12b_2$. In some embodiments, the method may comprise braiding the first plurality of collagen fibers $12b_1$ at about 5 PPI, braiding the second plurality of collagen fibers $12b_2$ at about 15 PPI, and braiding the third plurality of collagen fibers $12b_3$ at about 20 PPI.

In some embodiments, the method may comprise the first plurality, second plurality, and/or third plurality of braided collagen fibers $12b_1$, $12b_2$, $12b_3$ being braided in a repeating and/or alternating braid pattern. In some embodiments, the method may comprise the first plurality, second plurality, and/or third plurality of braided collagen fibers $12b_1$, $12b_2$, $12b_3$ being braided in a pattern in which each collagen fiber 12 of the first, second, and/or third plurality $12b_1$, $12b_2$, $12b_3$ passes over one collagen fiber 12 and then passes under one collagen fiber 12, each of which is repeated. In some embodiments, the method may comprise the first plurality, second plurality, and/or third plurality of braided collagen fibers $12b_1$, $12b_2$, $12b_3$ being braided in a repeating braid pattern in which each collagen fiber 12 of the first, second, and/or third plurality $12b_1$, $12b_2$, $12b_3$ passes over two collagen fibers 12 and then passes under two collagen fibers 12, each of which is repeated. The method may encompass the first, second, and/or third plurality of braided collagen fibers $12b_1$, $12b_2$, $12b_3$ passing over and under one or more collagen fibers 12 (e.g., 1, 2, 3, 4, 5 or more).

In some embodiments, the method may include the first plurality, second plurality, and/or third plurality of braided collagen fibers $12b_1$, $12b_2$, $12b_3$ comprising paired collagen fibers 12 arranged in a braid pattern or non-paired collagen fibers 12 arranged in a braid pattern.

In some embodiments, the method may include the first, second, and/or third plurality of braided collagen fibers $12b_1$, $12b_2$, $12b_3$ comprising at least one chase fiber 32 and/or at least one tri-axe fiber 34.

In some embodiments, the first plurality of collagen fibers $12p_1$, which may optionally be braided collagen fibers $12b_1$, may be held in tension while the second plurality of braided collagen fibers $12b_2$ is being braided around the first plurality of collagen fibers $12p_1$. As tension is applied, the collagen fibers $12p_1$ stretch. The change in length of the collagen fibers $12p_1$ in response to the tension that is applied can be indicated as a percentage of the original length of the plurality of collagen fibers $12p_1$. For example, in some embodiments, the first plurality of collagen fibers $12p_1$ may be held at a tension of about 5%, 10% or 15% to about 20%, 25% or 30% of the original length of the plurality of collagen fibers $12p_1$ while the second plurality of braided collagen fibers $12b_2$ is being braided around the first plurality of collage fibers $12p_1$. In some embodiments, the first and/or second plurality of braided collagen fibers $12b_1$, $12b_2$ may be held in tension while the third plurality of braided collagen fibers $12b_3$ is braided around the second plurality of braided collagen fibers $12b_2$. The first and/or second plurality of collagen fibers $12b_1$, $12b_2$ may be held at a tension of about 30%, 35%, 40%, 45%, 50%, 55%, 60% or 65% to about 70%, 75%, 80%, 85%, 90%, 95% or 100% while the third plurality of braided collagen fibers $12b_3$ is braided around the second plurality of braided collagen fibers $12b_2$.

In some embodiments, the method may further comprise attaching a needle 50 to at least one end of a construct 10.

Figure 12:
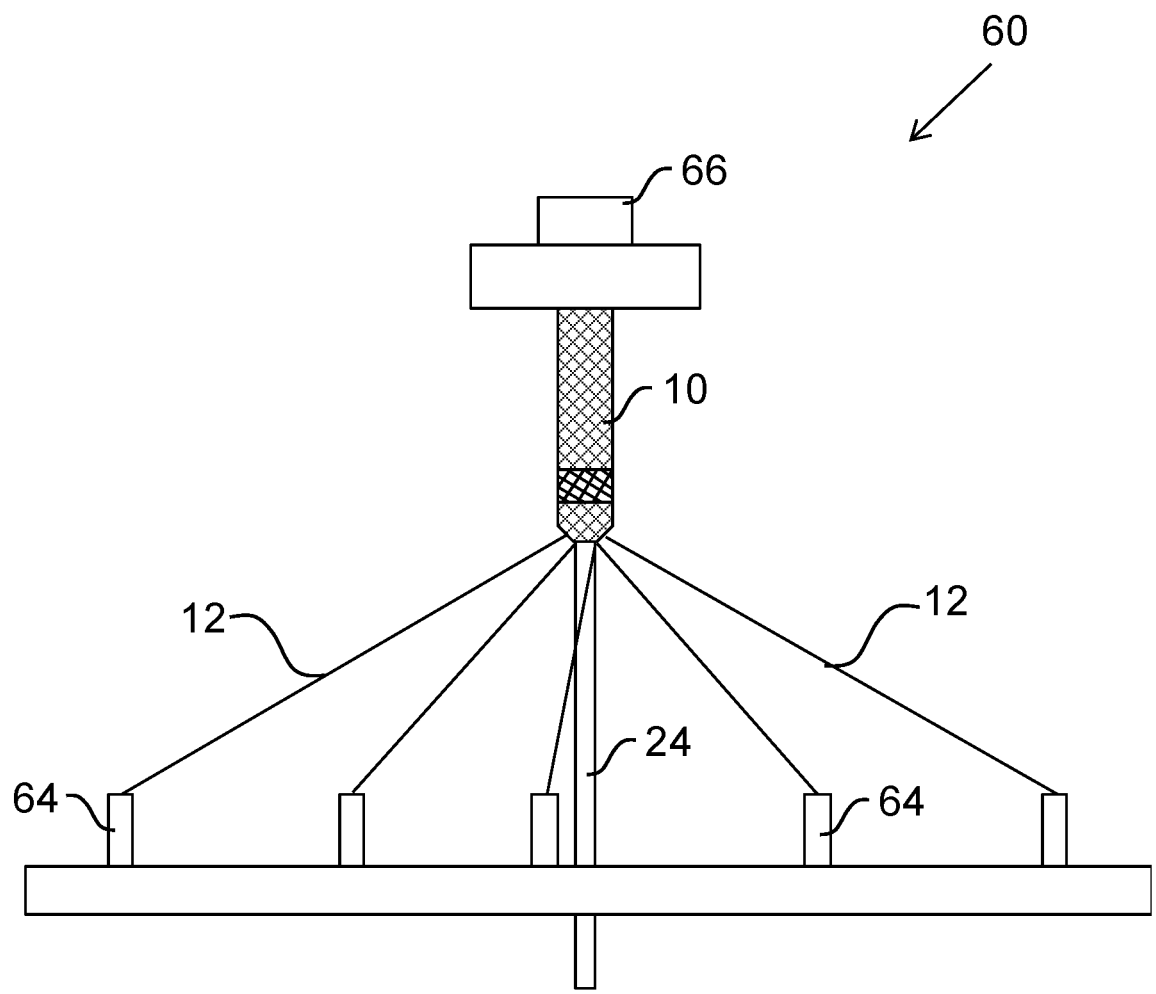
FIG. 12 is an illustration of an example automated braiding system according to further embodiments of the present invention.
Figure 13A:
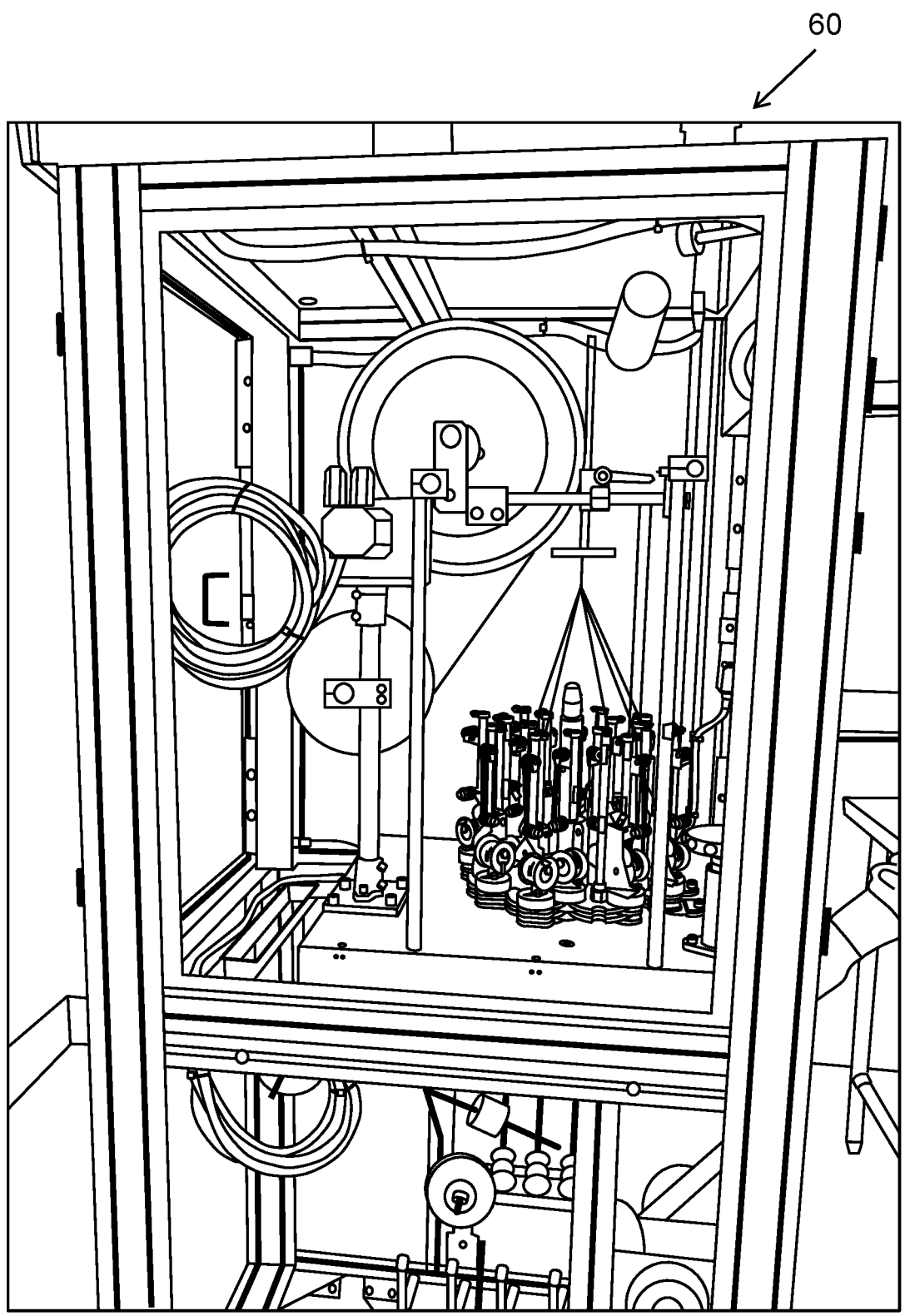
FIGS. 13A-13C are digital images of the example automated braiding system of FIG. 12 in operation.
Figure 13B:
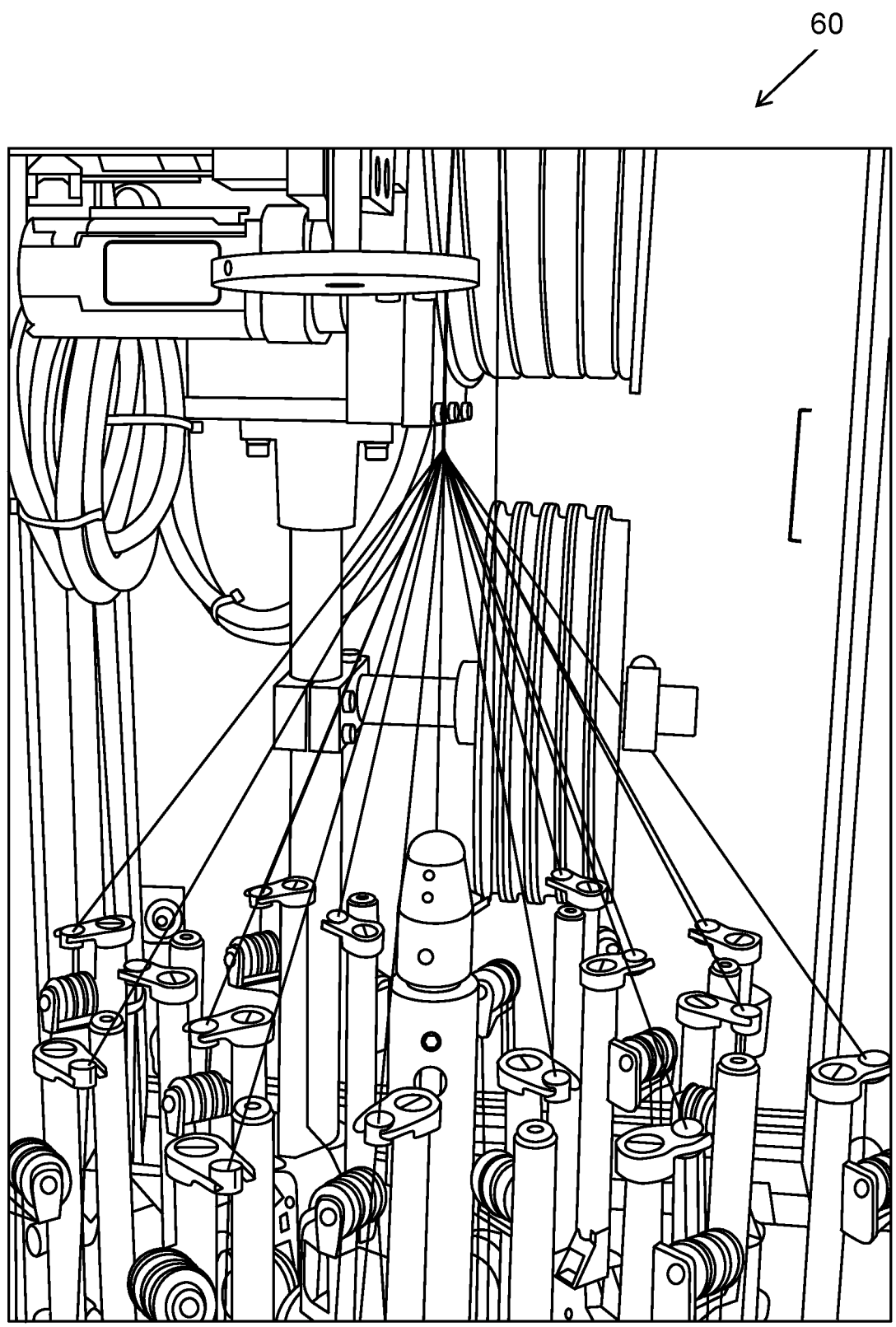
Figure 13C:
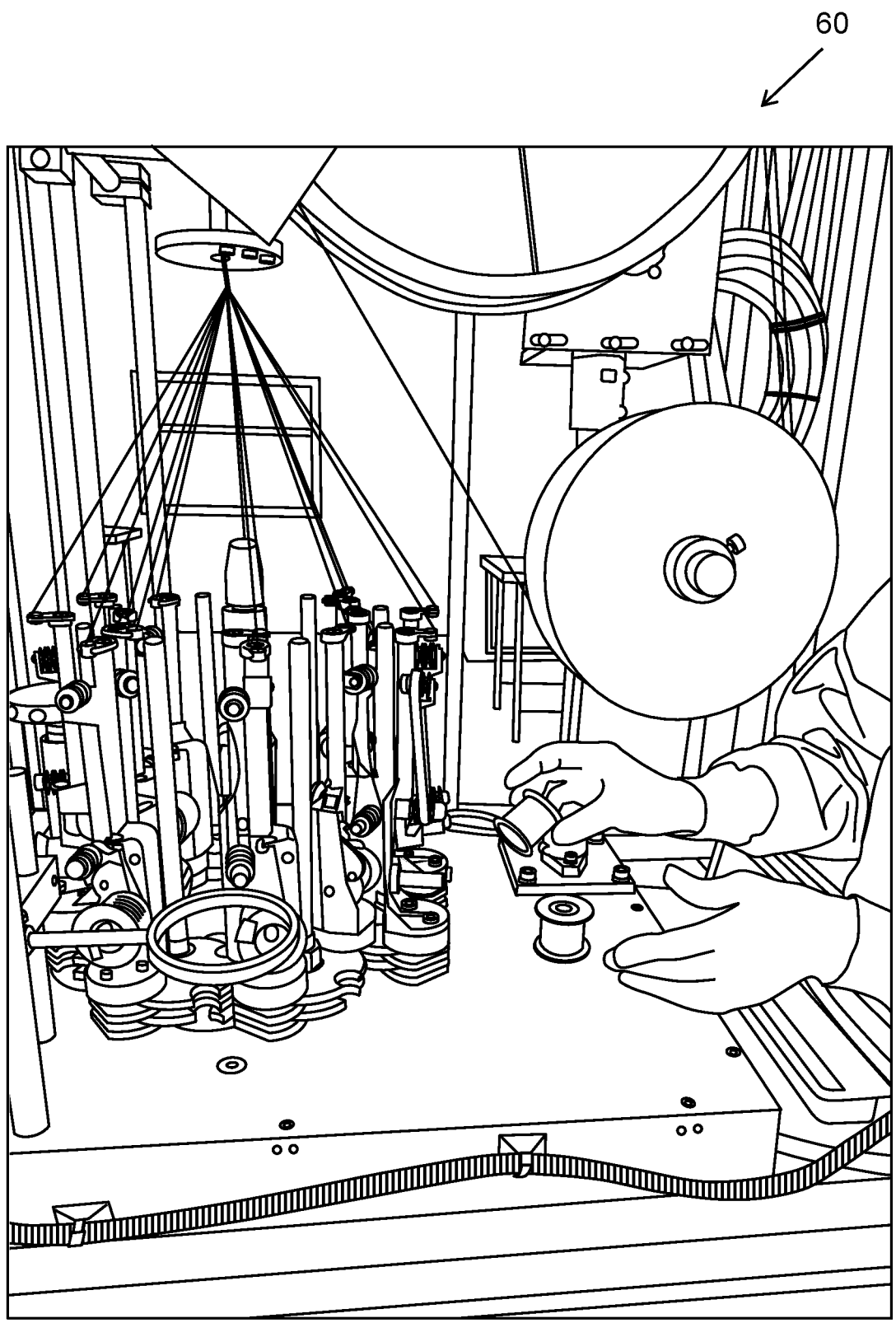

FIG. 12 illustrates an example of an automated braiding system 60 that may be used to form a construct 10 of the present invention. The system 60 may include a base 62, supporting spindles 64, and a braid puller 66. FIGS. 13A-13C are digital images of an example automated braiding system 60 in operation according to some embodiments of the present invention.

Figure 14:
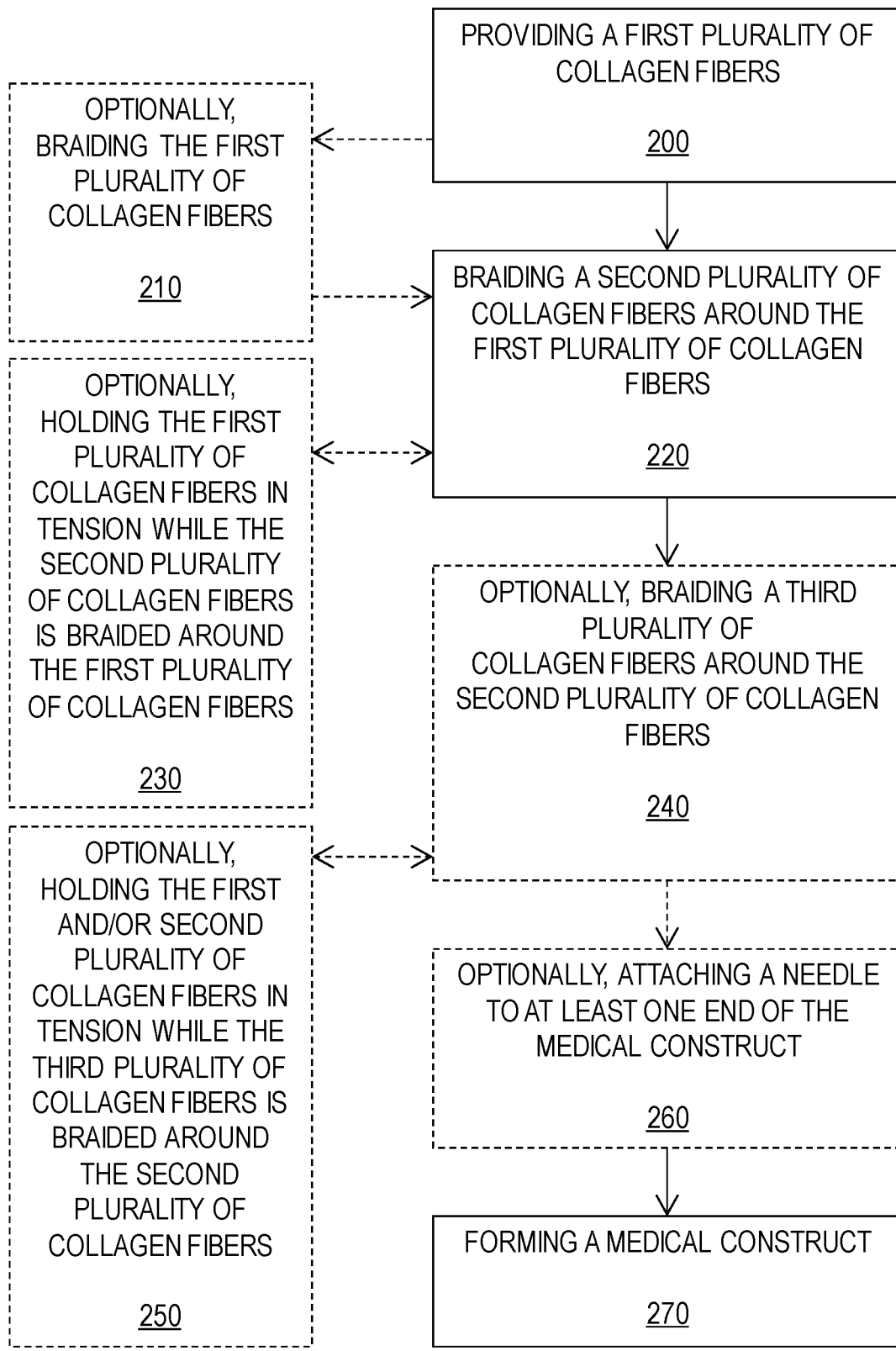
FIG. 14 is a flow chart of example operations that may be used to fabricate a construct according to embodiments of the present invention.

FIG. 14 is a flow chart of operations that may be used to carry out embodiments of the present invention. In some embodiments, a first plurality of collagen fibers may be provided (block 200). Optionally, the first plurality of collagen fibers may be braided (block 210). A second plurality of collagen fibers may be braided around the first plurality of collagen fibers (block 220) forming a construct (block 270).

Optionally, the first plurality of collagen fibers may be held in tension while the second plurality of collagen fibers is braided around the first plurality of collagen fibers (block 230). Optionally, a third plurality of collagen fibers may be braided around the second plurality of collagen fibers (block 240). Optionally, the first and/or second plurality of collagen fibers may be held in tension while the third plurality of collagen fibers is braided around the second plurality of collage fibers (block 250). Optionally, a needle may be attached to at least one end of the construct (block 260).

Figure 15A:
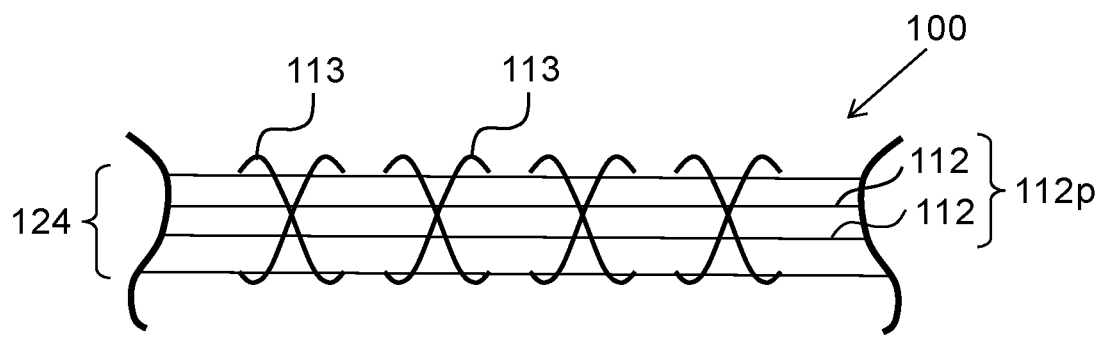
FIG. 15A is an illustrated side view of a suture according to further embodiments of the present invention.
Figure 15B:
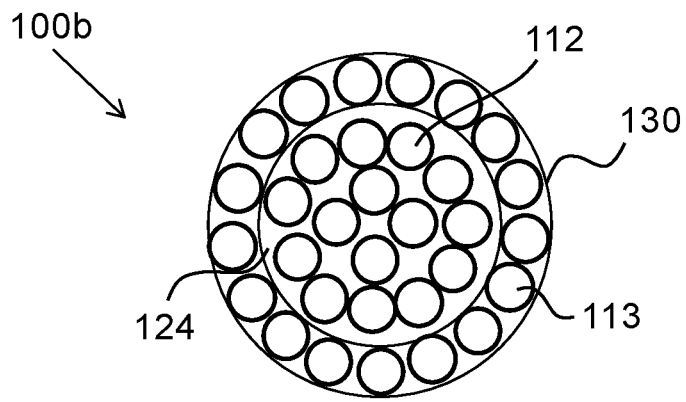
FIG. 15B is an illustrated end view of the suture of FIG. 15A.

A suture 100 (e.g., a medical suture) according to further embodiments of the present invention is illustrated in FIGS. 15A and 15B. The suture 100 may comprise a cylindrical body $100b$. The cylindrical body $100b$ of the suture 100 may comprise a core 124 and a layer 130 surrounding the core 124. The core 124 may comprise a plurality of collagen fibers 112. The layer 130 may comprise at least two collagen fibers 113. The collagen fibers 113 may be continuous length collagen fibers. The collagen fibers 113 forming layer 130 may be braided together. A core 124 and/or layer 130 of the suture 100 may comprise about 1, 5, or 10 collagen fibers 112 to about 15, 20, or 25 collagen fibers 112. For example, in some embodiments, the core 124 may comprise 4 collagen fibers 112 and the layer 130 may comprise 16 collagen fibers 113.

In some embodiments, the plurality of collagen fibers 112 that comprise the core 124 may extend substantially parallel to each other along a longitudinal axis (A) of the core 124. In some embodiments, the plurality of collagen fibers 112 forming the core 124 may be braided together. Collagen fibers 112, 113 forming the core 124 and/or layer 130 may be braided at about 5, 10, 15, or 20 PPI to about 25, 30, 35 or 40 PPI.

Figure 16:
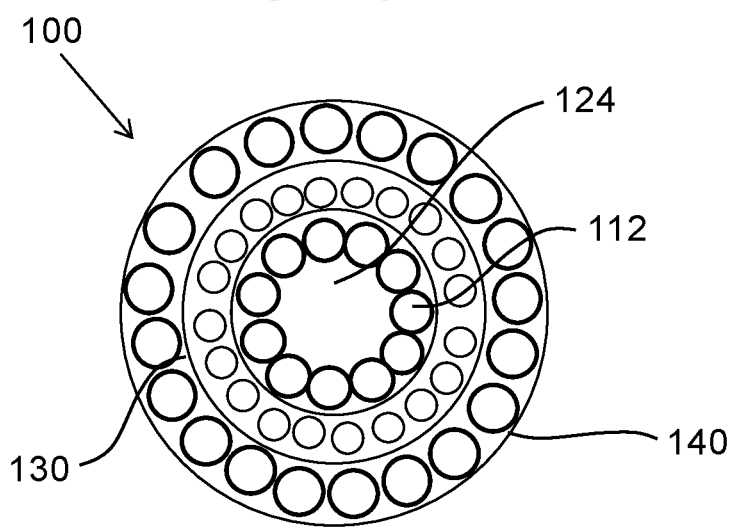
FIG. 16 is an illustrated end view of the suture of FIG. 15A with a second layer braided around the core according to some embodiments of the present invention.

In some embodiments, layer 130 of the suture 100 may be a first layer 130. As shown in FIG. 16, the suture 100 may comprise a second layer 140 that surrounds the core 124 and the first layer 130. A layer of a suture of the present invention (e.g., a first layer 130 and/or second layer 140) may each comprise at least two collagen fibers 112, which may be continuous length collagen fibers. The collagen fibers 112 in the first layer 130 may be braided together to form the core 124 and the collagen fibers 112 in the second layer 140 may be braided together around the core 124 and the first layer 130. In some embodiments, the core 124 of collagen fibers 112 may be braided at about 5 PPI, the first layer 130 of collagen fibers 112 may be braided at about 15 PPI, and the second layer 140 of collagen fibers 112 may be braided at about 20 PPI.

A core 124 of the suture 100 may comprise about 2, 4, 6, 8, or 10 to about 12, 14, 16, 18 or 20 collagen fibers 112. A first layer 130 of the suture 100 may comprise about 10, 12, or 14 to about 16, 18 or 20 collagen fibers 112. A second layer 140 of the suture 100 may comprise about 10, 12, or 14 to about 16, 18 or 20 collagen fibers 112. For example, in some embodiments, the core 124 may comprise 12 collagen fibers 112, the first layer 130 may comprise 16 collagen fibers 112, and the second layer 140 may comprise 16 collagen fibers 112. A suture 100 of the present invention may comprise about 10, 15, 20, 25, 30, or 35 to about 40, 45, 50, 55 or 60 collagen fibers 112.

At least a portion of the collagen fibers 112 of a suture 100 of the present invention (e.g., collagen fibers 112 in the core 124, first layer 130 and/or second layer 140) may have a tensile strength of about 0.5, 1, 1.5, 2, or 2.5 N to about 3, 3.5, 4, 4.5 or 5 N. For example, in some embodiments, the collagen fibers 112 in the core 124, first layer 130, and/or second layer 140, on average, may have a tensile strength of about 1.5, 1.75, 2, 2.25, or 2.5 N to about 2.75, 3, 3.25 or 3.5 N. A suture 100 of the present invention may have an overall tensile strength of about 10, 15, 20, or 25 N to about 30, 35, 40, 45 or 50 N.

In some embodiments, the suture 100 may further comprise at least one needle 50 attached to at least one end of the cylindrical body 100b. In some embodiments, the suture 100 may comprise a coating applied to the core 124, the first layer 130, and/or the second layer 140. In some embodiments, the coating comprises polylactic acid.

A suture 100 of the present invention may have a diameter of about 0.1, 0.25, 0.5, or 0.75 mm to about 1, 1.25 or 1.5 mm and have a length of about 30, 40, 50, or 60 cm to about 70, 80, 90, or 100 cm. The collagen fibers 112 that comprise a suture of the present invention may have a length of about 40, 50, or 60 cm to about 70, 80, 90, or 100 cm. A suture 100 of the present invention may have a flexural stiffness of about $1 \times 10^6$, $2 \times 10^6$, or $3 \times 10^6$ kg/cm2 to about 0.5, 0.75, or 1 kg/cm$^2$.

The present subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the presently claimed subject matter.

Example 1: A Chronic GLP Study to Evaluate the Resorption of a Cross-Linked Human Placenta Derived Collagen Suture (CollaFix) in a Rat Muscle Implant Model Purpose/Objective. The purpose of this study was to evaluate the resorption profile of the CollaFix suture over time in a rat muscle implant model.

Test/Control Articles. Test Article 01: CollaFix Size 0 Suture (a collagen suture made from purified collagen of human placental origin manufactured by MiMedx Group, Inc. comprising a 12 fiber core braided at 5PPI (layer 1), 16 fibers braided around layer 1 at 15PPI (layer 2), 16 fibers braided around layer 2 at 20PPI (layer 3)), Test Article 02: CollaFix Size 3-0 Suture (a collagen suture made from purified collagen human placental origin manufactured by MiMedx Group, Inc. comprising 4 parallel fibers as the core (layer 1) and 16 fibers braided around the core (layer 2) at 33PPI), Control Article 01: Plain Gut (Covidien plain gut suture size 0), Control Article 02: Plain Gut (Covidien plain gut suture size 3-0).

Methods. Animals were implanted with ~1.5 cm long pieces of CollaFix Suture (Size 0 or Size 3-0) in the right medial gluteal muscle and ~1.5 cm long pieces of Plain Gut Suture (Size 0 or Size 3-0) in left medial gluteal muscles. Animals were terminated on Day 14±2, 28±2, 42±3, 56±3, 63±3, and 77±3 days post implantation. Tissue response and resorption profiles of the CollaFix suture over time were evaluated.

Results and Conclusion. Each animal was implanted with both test and control article that were same in size (size 0 or 3-0). Test article was always implanted on the right side and control article was implanted on the left side. Overall, animals were in good health over the course of the study. No adverse clinical observations were believed to be test or control article related.

Control Article (C1, Plain Gut 0 Suture): The implant material was surrounded by a thin capsule at all the time points. Intracapsular/capsular inflammation increased throughout the duration of the study. Bioresorption of the implanted material also increased over time, which was additionally associated with increased cellular infiltration into the implant material. Bioresorption was initially observed as little to extensive at 56 day time point and was mild to extensive at the 77 day time point.

Test Article (T1, CollaFix Size 0 Suture): The implant material was surrounded by a thin capsule at all the time points. Intracapsular/capsular inflammation ranged from moderate to severe at all the time points. Bioresorption of the implanted material also increased over time, which was additionally associated with increased cellular infiltration into the implant material. Bioresorption was initially observed as little to moderate at 56 day time point and was mild to extensive at the 77 day time point.

Control Article (C2, Plain Gut 3-0 Suture): The implant material was surrounded by a thin capsule at all the time points. Intracapsular/capsular inflammation increased throughout the duration of the study. Bioresorption of the implanted material also increased over time, which was additionally associated with increased cellular infiltration into the implant material. Bioresorption was initially observed as little to moderate at 56 day time point and was mild to moderate at the 77 day time point.

Test Article (T2, CollaFix Size 3-0 Suture): The implant material was surrounded by a thin capsule at all the time points. Intracapsular/capsular inflammation ranged from mild to severe at all the time points. Bioresorption of the implanted material also increased over time, which was additionally associated with increased cellular infiltration into the implant material. Bioresorption was initially observed as little to mild at 42 day time point and was mild to extensive at the 77 day time point.

Test System Justification. Intramuscular implantation has been studied extensively in rats, and is an approved model for muscle implant test among the regulatory bodies. The current review of the literature indicates animal models are currently in use for evaluation of muscle implant test. The rat model is well defined and described in the literature and in the regulations.

A total of 72 (plus 4 backup animals) were eligible to be enrolled for the intramuscular implantation test at APS. There were 6 animals per test article per group. Test article size 0 and size 3-0 were tested in this study. This study was a formal GLP study.

Implant or Treatment Procedure Results. Each animal was implanted with both test and control article that were same in size (size 0 or 3-0). Test article was always implanted on the right side and control article was implanted on the left side. A skin cut down was performed on left and right site of the lower back to explore the gluteal muscle on both sides. After locating the gluteal muscle, a 14-gauge catheter (test and control article size 0) or an 18-gauge needle (test and control article size 3-0) was used for to poke through the center of medial gluteal muscle (insert the needle into the muscle caudally and proceeding cranially). Test and control articles were cut to approximately 1.5 cm in length. The test or control article suture was inserted from the tip of the needle. While holding the suture from the tip of the needle, the needle was then pulled back to leave the test article in the muscle. A knot was tied using 4-0 prolene suture at the cranial end of the implant (about 0.5 cm away from the implant site) to mark the implant site.

Termination Procedure Results. All animals were euthanized at their scheduled termination date and transferred to necropsy for gross examination and tissue procurement.

Animal Health Results. In accordance with the protocol, each animal's health was monitored daily for signs of abnormalities. When necessary following the implant procedure, all animals were administered analgesics (Buprenorphine) per protocol to help control pain. Per protocol, incision checks were performed daily for 5 days. All animals were in overall good health over the course of the study with the following exceptions. On study day 12, animal 164286 in group 6a had a patch of dry scabbing at the base of tail with mild erythema. Animals appeared normal otherwise. On study day 9, animal 164426 in group 1a had an approximately 1.0×1.0 cm moist scab on the left dorsal side of the base of tail with mild erythema. The scab at the base of the tail was healing normally with no erythema observed. No adverse clinical observations were believed to be test or control article related.

Gross Necropsy Results. There were no abnormal necropsy findings for this study.

Example 2: CollaFix Suture Tensile Strength Testing for Porcine Dermis Explants

Purpose. The purpose of this study was to evaluate the strength and tensile characteristics of repaired porcine full thickness dermal wounds sutured closed using either 3-0 CollaFix (a collagen suture made from purified collagen human placental origin manufactured by MiMedx Group, Inc. consisting of 4 parallel fibers as the core (layer 1) and 16 fibers braided around the core (layer 2) at 33PPI), 3-0 Vicryl, or 3-0 Plain Gut suture.

Summary. This report provides details on the strength of explanted full thickness porcine dermal wounds sutured closed using either 3-0 CollaFix, 3-0 Vicryl, or 3-0 Plain Gut suture. These samples were obtained at the following time points: t=0, t=7 days, t=14 days, and t=28 days. The peak tensile strength of the samples were obtained to characterize the strength of the repairs. Samples were obtained from full thickness dermal closures performed in a porcine model per T3 protocol SX20P entitled Non-GLP Evaluation of Cosmetic Appearance and Strength of a Cross-linked Human Placenta Derived Collagen Suture (CollaFix) in a Porcine Full Thickness Dermal Repair Model. Each incision was 4 cm wide with a 3 cm portion sutured using a continuous intradermal suture pattern utilizing 3 full passes with either 3-0 CollaFix, 3-0 Vicryl, or 3-0 Plain Gut suture. On either side of the continuous suture, 3-0 Prolene was used to suture the remainder of the incision using 2 interrupted sutures per side, or 4 interrupted sutures per incision.

Upon explant, the samples were placed on ice and tested within 8 hours of termination using an Instron mechanical testing machine. Prior to testing, the Prolene sutures were removed to ensure that only the strength of the continuously sutured region was evaluated. The results indicated that at the t=0 and 28 day time points, there was no significant difference between any of the suture types with average values ranging from 47.045N to 92.586N at t=0 and 249.339N and 274.212N at 28 days. At 7 days, the Vicryl suture was the strongest ($p<0.05$) with a value of 86.270N, and at 14 days, the CollaFix suture was the strongest ($p<0.01$) with a value of 169.671N.

Materials/Equipment. INSTRON Series 5560 Load Frame, INSTRON Series 2525-800 Calibrated Load Cell, 500N Capacity±0.25%, INSTRON Series 2712-017 5 kN Pneumatic Grips, Tweezers, Calibrated Ruler, 1 kilogram Calibrated Weight, 500 gram Calibrated Weight, Thin Tip Permanent Marker, and Nitrile Gloves.

Procedure. Execute the following steps to prepare the INSTRON for testing:

Attach the 500 N capacity load cell to the INSTRON for testing per section 6-13 of the Reference Manual for INSTRON Series 5500 Load Frames, Series 5560—Installation of a Series 2525 Load Cell.

Visually inspect the load cell before performing any tests, looking for signs of corrosion, cable damage, or mechanical misalignment. In order to prevent overload, first connect the sensor and then screw the load cell into place. If the load cell appears to be damaged or compromised in any way, contact an operations manager and quality assurance for equipment evaluation and possible re-calibration or replacement.

Figure 17:
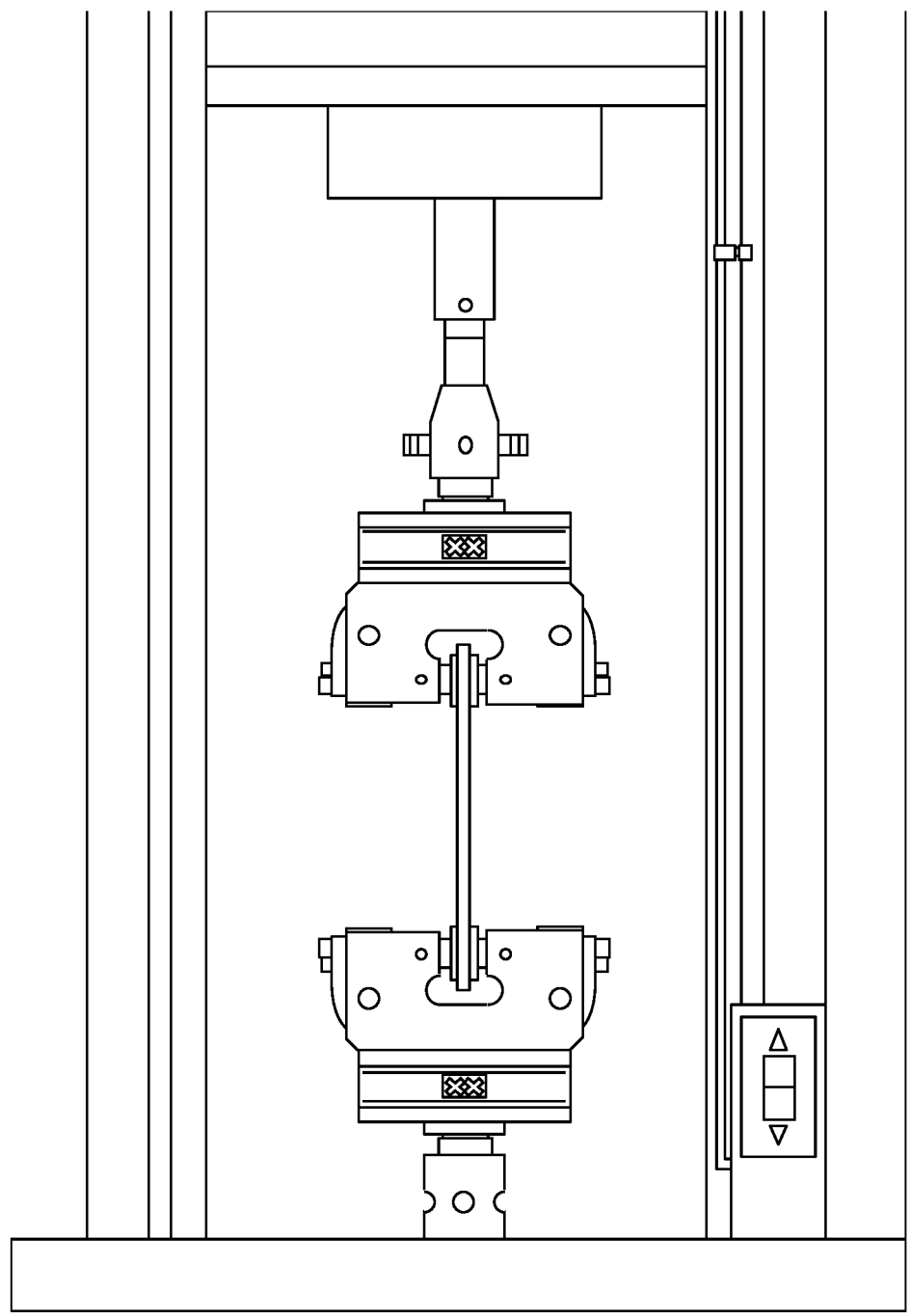
FIG. 17 is an illustration showing the orientation of the pneumatic grips of an INSTRON device used to test the tensile strength of the construct according to some embodiments of the present invention.

Install the pneumatic grips in the orientation shown in FIG. 17. Both compressed air inputs should be on the left side if facing the INSTRON.

Perform the following steps to ensure the INSTRON load cell and pneumatic grips are operating properly. Set the pneumatic grip pressure regulator to 35±5 psi. Actuate the grips pneumatic grips using the pneumatic footswitch to ensure the pressure is maintained and stable. Adjust the pressure if necessary. Open the pneumatic grips using the adjusting screws and set the position of the jaw fasces to a 6 as indicated on the grip face holder. Adjust the distance between the top and bottom pneumatic grips so that they are separated by approximately 20 cm. Adjustment can be made using the jog up/jog down buttons found on the physical INSTRON control panel. Hang approximately 6 inches of string from the top pneumatic grip and zero out the load cell to 0.000 N. Release the string from the pneumatic grip by pressing the footswitch. Using a gloved hand, hang a 500 gram calibrated weight using approximately 6 inches of string from the top pneumatic grip. Record the value displayed on load output of the software. The value should be 1.1023±0.0220 lbs. If the value displayed is beyond this range, contact an operations manager or quality assurance. Using a gloved hand, remove the 500 gram calibrated weight and store it back in its packaging. Using a gloved hand, hang a 1 kilogram calibrated weight using approximately 6 inches of string from the top pneumatic clamp. Record the value displayed. The value should be 2.20463±0.0441 lbs. If the value displayed is beyond this range, contact an operations manager or quality assurance. Using a gloved hand, remove the 1 kilogram calibrated weight and store it back in its packaging. Adjust the distance between the top and bottom pneumatic grips so that they are separated by approximately 85 mm. Confirm the distance using a calibrated ruler. Reset the gauge length to show 0.0000 mm.

Execute the following steps to prepare the test apparatus: Using tweezers, insert one end of the sample into the upper grip. Ensure that at least 7 mm of the sample is in the grip. Close the pneumatic grip onto the sample. Lower the upper grip until at least 7 mm of the sample is in the lower grip. Using tweezers, ensure that the bottom part of the sample in in the lower grip. Ensure that at least 7 mm of the sample is in the grip. Ensure that the dermal repair site is approximately midway between the upper and lower grip. Close the pneumatic grip onto the sample. Zero out the load cell to show 0.000 N. Measure and record the gauge length to the nearest whole millimeter using a calibrated ruler. The gauge length for this test is the distance between the bottom of the upper clamp and the top of the lower clamp.

For performing tensile testing and data collection; the speed of the upper grip shall be set at 50 mm/min. The sample should be placed in tension and be stressed to failure. At the point of failure, the INSTRON should cease movement and the sample should break in two. If failure is observed, measure and record the gauge length to the nearest whole millimeter using a calibrated ruler. If failure is not observed and the sample pulls out of the grips at either end: Stop the test and save the data generated. Discard the sample and record that the sample failed to break. Prepare additional samples to fulfill the required sample size.

Figure 18:
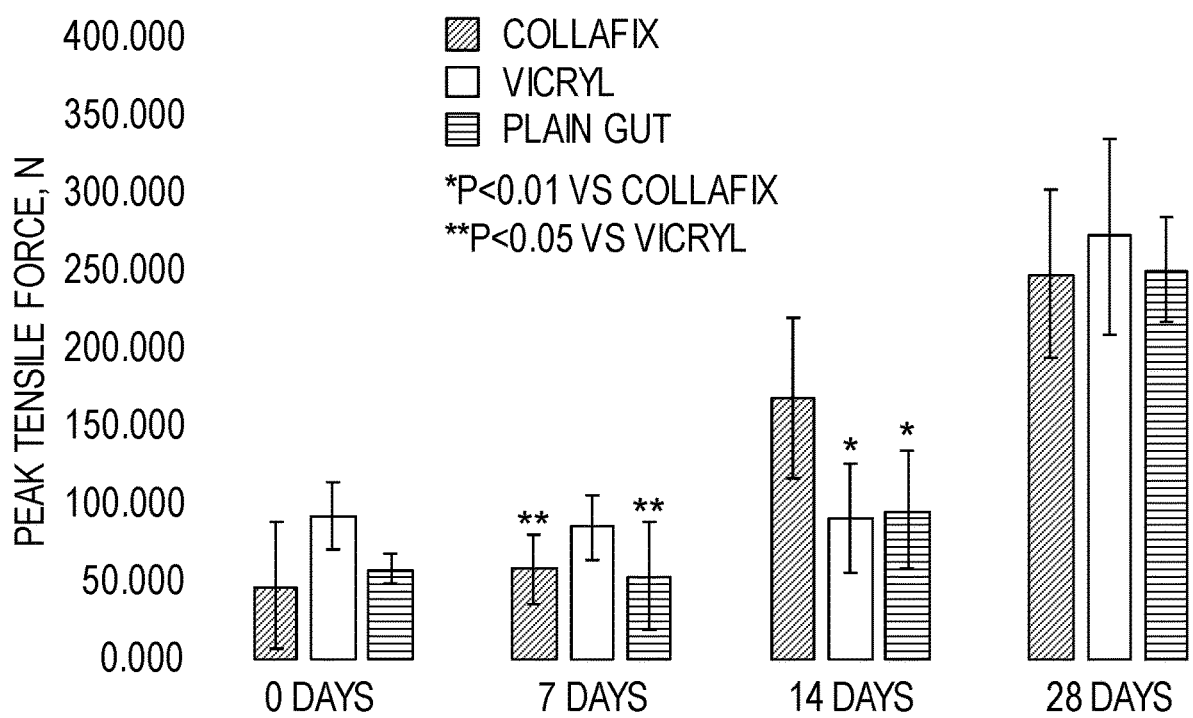
FIG. 18 is a graph showing peak tensile strength results of the porcine dermal closures over time.

Results. A summary of the results at each time point is presented in Table 1 and FIG. 18.

TABLE 1

Summary of Peak Tensile Results (N, Newtons)

| Time point | CollaFix Average | CollaFix Std Dev | Vicryl Average | Vicryl StdDev | Plain Gut Average | Plain Gut StdDev |
|---|---|---|---|---|---|---|
| 0 days | 47.045 | 41.880 | 92.586 | 21.609 | 59.046 | 9.815 |
| 7 days | 59.592 | 21.687 | 86.270 | 20.454 | 54.970 | 34.545 |
| 14 days | 169.671 | 51.175 | 93.038 | 34.570 | 98.234 | 37.386 |
| 28 days | 249.339 | 53.436 | 274.212 | 62.849 | 252.670 | 34.160 |

While some temporal differences in peak tensile strength at 7 days in which Vicryl closed incisions were significantly stronger and at 14 days in which CollaFix closed incisions were significantly stronger, there was no significant difference in peak tensile strength between CollaFix, Vicryl, and Plain Gut at t=0 or at 28 days.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A construct, comprising:
    a cylindrical body that comprises a first layer that is a core of the construct and a second layer that circumferentially surrounds the core,
    wherein the core comprises fibers that consist of collagen fibers and wherein the core has 2 to 20 collagen fibers that are parallel to each other along a longitudinal axis of the core or that are braided together;
    wherein the second layer comprises a plurality of collagen fibers that are braided together and that circumferentially surround and contact the core and,
    wherein the construct has a diameter in a range of about 0.1 to about 0.5 mm and has a tensile strength in a range of about 10 N to about 50 N.

2. The construct of claim 1, further comprising a needle attached to at least one end of the construct.

3. The construct of claim 1, wherein each collagen fiber of the score extends substantially parallel to each other along the longitudinal axis of the core.

4. The construct of claim 1, wherein the 2 to 20 collagen fibers of the core are braided together.

5. The construct of claim 4, wherein the braided collagen fibers of the core and/or the plurality of collagen fibers of the second layer are braided in a repeating braid pattern in which each collagen fiber thereof passes over only one collagen fiber and under only one collagen fiber.

6. The construct of claim 4, wherein the braided collagen fibers of the core and/or the plurality of collagen fibers of the second layer are braided in a repeating braid pattern in which each collagen fiber thereof passes over only two collagen fibers and under only two collagen fibers.

7. The construct of claim 4, wherein the braided collagen fibers of the core and/or the plurality of collagen fibers of the second layer comprises paired collagen fibers.

8. The construct of claim 4, wherein the braided collagen fibers of the core and/or the plurality of collagen fibers of the second layer are arranged in an alternating braid pattern.

9. The construct of claim 4, wherein the braided collagen fibers of the core and/or the plurality of collagen fibers of the second layer comprise a first, second, and third collagen fiber arranged with the second collagen fiber being in between the first and third collagen fibers, and the first, second and third collagen fibers are braided together to form a braid, wherein the braid comprises a portion in which the first and second collagen fibers form a pick under a crossing collagen fiber, and the third collagen fiber passes over the crossing collagen fiber, and a portion in which the second and third collagen fibers form a pick under the crossing collagen fiber, and the first collagen fiber passes over the crossing collagen fiber.

10. The construct of claim 9, wherein the first and third collagen fibers are arranged in an alternating braid pattern.

11. The construct of claim 4, wherein the braided collagen fibers of the core have a picks per inch (PPI) that is greater than the PPI of the plurality of braided collagen fibers of the second layer.

12. The construct of claim 1, further comprising a third layer, the third layer comprising a plurality of braided collagen fibers, wherein said third layer circumferentially surrounds the first layer and the second layer.

13. The construct of claim 12, wherein the 2 to 20 collagen fibers of the core are braided together at about 5 PPI, the plurality of collagen fibers of the second layer are braided together at about 15 PPI, and the plurality of braided collagen fibers of the third layer are braided together at about 20 PPI.

14. The construct of claim 1, wherein the construct comprises about 10 to about 60 collagen fibers.

15. The construct of claim 1, wherein the plurality of collagen fibers of the second layer comprise about 10 to about 20 collagen fibers that are braided in a repeating braid pattern in which each collagen fiber of the plurality of collagen fibers of the second layer passes over only one collagen fiber and under only one collagen fiber.

16. The construct of claim 1, wherein the construct has a flexural stiffness in a range of about $3\times10^6$ kg/cm$^2$ to about 1 kg/cm$^2$.

17. The construct of claim 1, further comprising a coating applied to the 2 to 20 collagen fibers of the core and/or to the plurality of collagen fibers of the second layer.

18. A method of manufacturing a construct, the method comprising:

providing a first plurality of fibers, wherein the first plurality of fibers consists of 2 to 20 collagen fibers that form a core of the construct, wherein the core comprises fibers that consist of the 2 to 20 collagen fibers and the 2 to 20 collagen fibers are parallel to each other along a longitudinal axis of the core or are braided together; and braiding a plurality of collagen fibers around the core, wherein the plurality of collagen fibers circumferentially surround and contact the core, thereby forming the construct, wherein the construct is cylindrical and has a diameter in a range of about 0.1 to about 0.5 mm, and wherein the construct has a tensile strength in a range of about 10 N to about 50 N.

19. A medical suture, comprising:

a cylindrical body, the cylindrical body comprising:

a core comprising fibers that consist of collagen fibers, wherein the core has 2 to 12 collagen fibers and the 2 to 12 collagen fibers of the core are parallel to each other along a longitudinal axis of the core or are braided together; and a layer that circumferentially surrounds the core, wherein the layer comprises about 10 to about 20 collagen fibers that are braided together around the core, wherein the medical suture comprises about 12 to about 60 collagen fibers, and wherein the medical suture has a diameter in a range of about 0.1 to about 0.5 mm and has a tensile strength in a range of about 10 N to about 50 N.

* * * * *